United States Patent [19]

Lynch et al.

[11] Patent Number: 5,766,943

[45] Date of Patent: Jun. 16, 1998

[54] DNA SEQUENCES FOR SOLUBLE FORM OF CD23

[75] Inventors: Richard G. Lynch, Iowa City, Iowa; Junji Yodoi, Kyoto, Japan; Rafael M. Nunez, Belp, Switzerland; Minoru Matsui, Kyoto, Japan

[73] Assignee: University of Iowa Research Foundation, Iowa City, Iowa

[21] Appl. No.: 365,103

[22] Filed: Dec. 28, 1994

Related U.S. Application Data

[63] Continuation-in-part of Ser. No. 931,142, Aug. 17, 1992, abandoned.

[51] Int. Cl.$^6$ ............................. C12N 15/13; C12N 5/10; C12N 15/63; C12N 1/21
[52] U.S. Cl. ................. 435/325; 435/320.1; 435/252.3; 536/23.5; 935/9
[58] Field of Search ........................... 435/69.1, 252.3, 435/320.1, 325; 935/66, 22, 9; 536/23.1, 23.5

[56] References Cited

FOREIGN PATENT DOCUMENTS 0286700  4/1987  European Pat. Off. .

OTHER PUBLICATIONS

Kikutani et al. Cell 47 (1986) 657–665.

Ikuta et al. PNAS 84 (1987) 819–823.

Ludin et al. EMBO J. 6(1987) 109–114.

Uchibayashi et al. J. Immunol. 142(1989) 3901–3908.

Gollnick et al. J. Immunol. 144(1990) 1974–1982.

Bettler et al. PNAS 86 (1989) 7566–7570.

*Primary Examiner*—Paula K. Hutzell
*Assistant Examiner*—Robert C. Hayes
*Attorney, Agent, or Firm*—Zarley, McKee, Thomte, Voorhees & Sease

[57] ABSTRACT

This invention discloses the isolation and purification of gene sequences which code upon expression a soluble form of the traditionally membrane bound immuno-regulatory protein, CD23. This protein regulates the amount of IgE present in the blood and upon cloning and amplification, procedures may be used in the treatment of IgE mediated diseases.

8 Claims, 17 Drawing Sheets

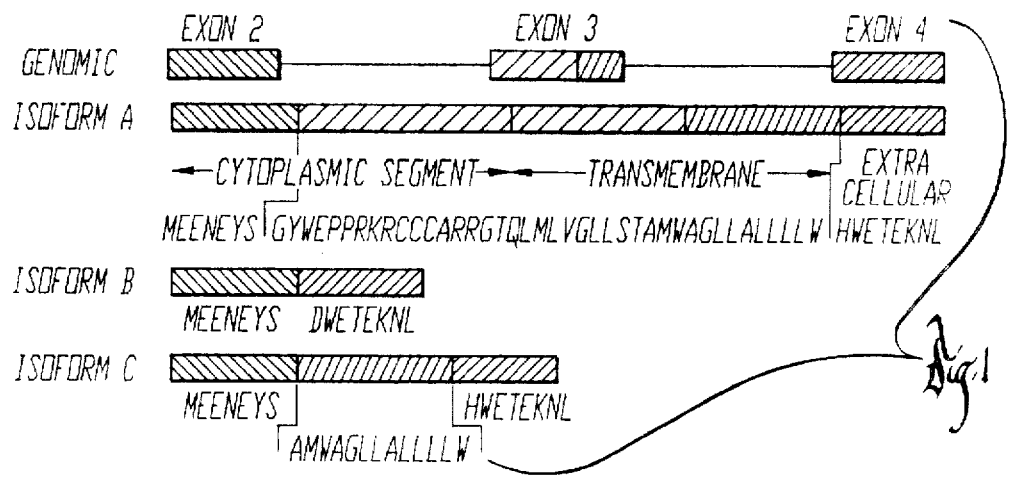
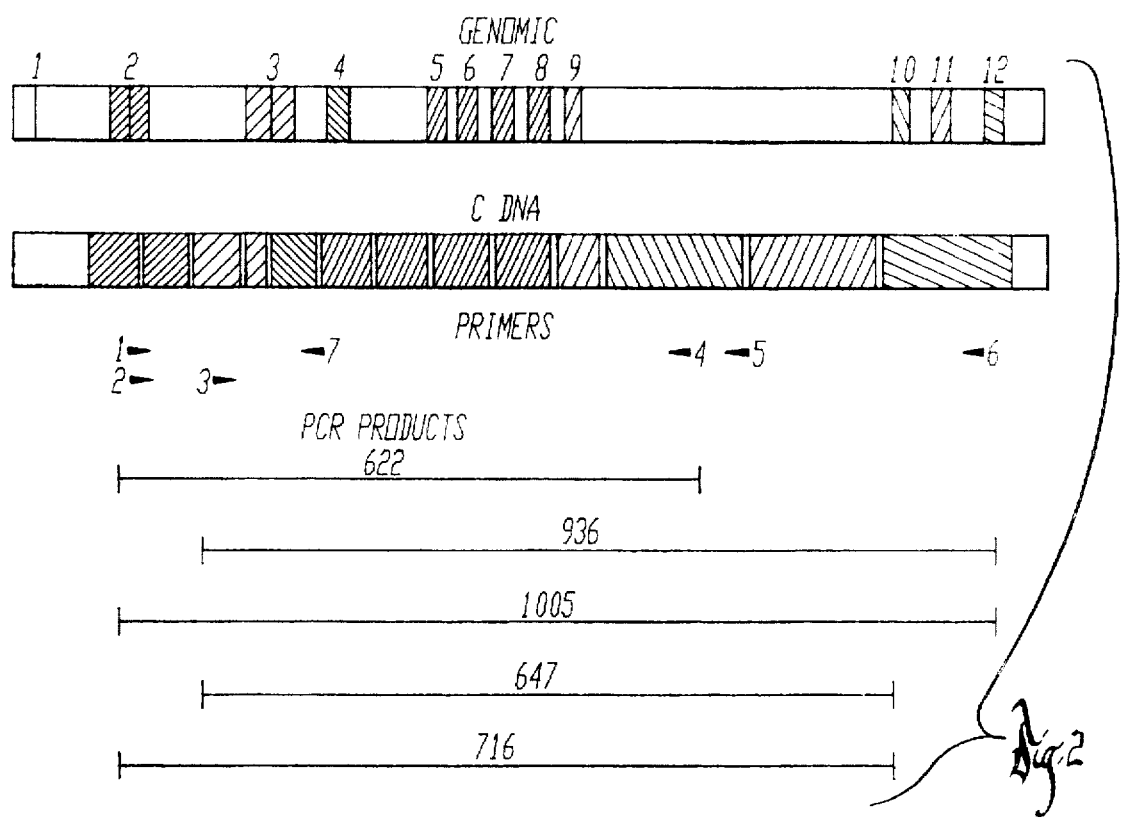

```
GGAAGGATCC AAACAAGACT GCC ATG GAA GAA AAT GAA TAC TCA:GGA TAC
                         Met Glu Glu Asn Glu Tyr Ser:Gly Tyr
                          1                   5

TGG GAA CCT CCT AGA AAG CGT TGC TGC TGT GCA AGA CGT GGG ACA CAG
Trp Glu Pro Pro Arg Lys Arg Cys Cys Cys Ala Arg Arg Gly Thr Gln
 10              15                  20                      25

CTC ATG TTG GTG GGG CTG CTG AGC ACA GCA ATG TGG GCT GGC CTG CTG
Leu Met Leu Val Gly Leu Leu Ser Thr Ala Met Trp Ala Gly Leu Leu
                 30                  35                      40

GCC CTG CTT CTT CTG TGG:CAC TGG GAA ACG GAG AAG AAT CTA AAA CAG
Ala Leu Leu Leu Leu Trp:His Trp Glu Thr Glu Lys Asn Leu Lys Gln
                 45              50                  55

CTG GGA GAC ACT GCA ATT CAG AAT GTC TCT CAT GTT ACC AAG GAC TTA
Leu Gly Asp Thr Ala Ile Gln Asn Val Ser His Val Thr Lys Asp Leu
         60                  65                  70

CAA AAA TTC CAG AGT AAT CAA TTG GCC CAG AAG TCC CAG GTT GTT CAG
Gln Lys Phe Gln Ser Asn Gln Leu Ala Gln Lys Ser Gln Val Val Gln
     75                  80                  85

ATG TCA CAA AAC TTG CAA GAA CTC CAA GCT GAA CAG AAG CAA ATG AAA
Met Ser Gln Asn Leu Gln Glu Leu Gln Ala Glu Gln Lys Gln Met Lys
 90                  95                 100                 105

GCT CAG GAC TCT CGG CTC TCC CAG AAC CTG ACC GGA CTC CAG GAG GAT
Ala Gln Asp Ser Arg Leu Ser Gln Asn Leu Thr Gly Leu Gln Glu Asp
                110                 115                 120

CTA AGG AAC GCC CAA TCC CAG AAC TCA AAA CTC TCC CAG AAC CTG AAC
Leu Arg Asn Ala Gln Ser Gln Asn Ser Lys Leu Ser Gln Asn Leu Asn
             125                 130                 135

AGA CTC CAA GAC GAT CTA GTC AAC ATC AAA TCC CTG GGC TTG AAT GAG
Arg Leu Gln Asp Asp Leu Val Asn Ile Lys Ser Leu Gly Leu Asn Glu
         140                 145                 150

AAG CGC ACA GCC TCC GAT TCT CTA GAG AAA CTC CAG GAA GAG GTG GCA
Lys Arg Thr Ala Ser Asp Ser Leu Glu Lys Leu Gln Glu Glu Val Ala
 155                 160                 165

AAG CTG TGG ATA GAG ATA CTG ATT TCA AAG GGA ACT GCA TGC AAC ATA
Lys Leu Trp Ile Glu Ile Leu Ile Ser Lys Gly Thr Ala Cys Asn Ile
170             175                 180                     185
```

Fig. 3A

```
TGT CCC AAG AAC TGG CTC CAT TTC CAA CAG AAG TGC TAC TAT TTT GGC
Cys Pro Lys Asn Trp Leu His Phe Gln Gln Lys Cys Tyr Tyr Phe Gly
            190             His     195                 200

AAG GGC TCC AAG CAG TGG ATC CAG GCC AGG TTC GCC TGC AGT GAC CTG
Lys Gly Ser Lys Gln Trp Ile Gln Ala Arg Phe Ala Cys Ser Asp Leu
            205             210                 215

CAA GGG CGA CTA GTC AGC ATC CAC AGC CAA AAG GAA CAG GAC TTC CTG
Gln Gly Arg Leu Val Ser Ile His Ser Gln Lys Glu Gln Asp Phe Leu
            220             225                 230

ATG CAA CAC ATC AAC AAG AAG GAT TCC TGG ATT GGC CTC CAG GAT CTC
Met Gln His Ile Asn Lys Lys Asp Ser Trp Ile Gly Leu Gln Asp Leu
            235             240                 245

AAT ATG GAG GGA GAG TTT GTA TGG TCG GAC GGG AGC CCT GTG GGT TAT
Asn Met Glu Gly Glu Phe Val Trp Ser Asp Gly Rer Pro Val Gly Tyr
250             255                 260                 265

AGC AAC TGG AAT CCA GGG GAG CCC AAT AAC GGG GGC CAG GGT GAG GAC
Ser Asn Trp Asn Pro Gly Glu Pro Asn Asn Gly Gly Gln Gly Glu Asp
            270             275                 280

TGT GTG ATG ATG CGG GGA TCC GGC CAG TGG AAC GAC GCC TTC TGC CGC
Cys Val Met Met Arg Gly Ser Gly Gln Trp Asn Asp Ala Phe Cys Arg
            285             290                 295

AGC TAC TTG GAT GCA TGG GTG TGT GAG CAG CTG GCA ACA TGT GAG ATA
Ser Tyr Leu Asp Ala Trp Val Cys Glu Gln Leu Ala Thr Cys Glu Ile
            300             305                 310

TCT GCC CCC TTA GCC TCT GTG ACT CCA ACA AGG CCC ACC CCA
Ser Ala Pro Leu Ala Ser Val Thr Pro Thr Arg Pro Thr Pro A
            315             320             325
```

Fig. 3B

```
GGAAGGATCC AAACAAGACT GCC ATG GAA GAA AAT GAA TAC TCA GAC TGG
                         Met Glu Glu Asn Glu Tyr Ser Asp Trp
                          1               5
```

| GAA | ACG | GAG | AAG | AAT | CTA | AAA | CAG | CTG | GGA | GAC | ACT | GCA | ATT | CAG | AAT |
|-----|-----|-----|-----|-----|-----|-----|-----|-----|-----|-----|-----|-----|-----|-----|-----|
| Glu | Thr | Glu | Lys | Asn | Leu | Lys | Gln | Leu | Gly | Asp | Thr | Ala | Ile | Gln | Asn |
| 10  |     |     |     |     | 15  |     |     |     |     | 20  |     |     |     |     | 25  |

| GTC | TCT | CAT | GTT | ACC | AAG | GAC | TTA | CAA | AAA | TTC | CAG | AGT | AAT | CAA | TTG |
|-----|-----|-----|-----|-----|-----|-----|-----|-----|-----|-----|-----|-----|-----|-----|-----|
| Val | Ser | His | Val | Thr | Lys | Asp | Leu | Gln | Lys | Phe | Gln | Ser | Asn | Gln | Leu |
|     |     |     |     | 30  |     |     |     |     | 35  |     |     |     |     | 40  |     |

| GCC | CAG | AAG | TCC | CAG | GTT | GTT | CAG | ATG | TCA | CAA | AAC | TTG | CAA | GAA | CTC |
|-----|-----|-----|-----|-----|-----|-----|-----|-----|-----|-----|-----|-----|-----|-----|-----|
| Ala | Gln | Lys | Ser | Gln | Val | Val | Gln | Met | Ser | Gln | Asn | Leu | Gln | Glu | Leu |
|     |     |     | 45  |     |     |     |     | 50  |     |     |     |     | 55  |     |     |

| CAA | GCT | GAA | CAG | AAG | CAA | ATG | AAA | GCT | CAG | GAC | TCT | CGG | CTC | TCC | CAG |
|-----|-----|-----|-----|-----|-----|-----|-----|-----|-----|-----|-----|-----|-----|-----|-----|
| Gln | Ala | Glu | Gln | Lys | Gln | Met | Lys | Ala | Gln | Asp | Ser | Arg | Leu | Ser | Gln |
|     |     | 60  |     |     |     |     | 65  |     |     |     |     | 70  |     |     |     |

| AAC | CTG | ACC | GGA | CTC | CAG | GAG | GAT | CTA | AGG | AAC | GCC | CAA | TCC | CAG | AAC |
|-----|-----|-----|-----|-----|-----|-----|-----|-----|-----|-----|-----|-----|-----|-----|-----|
| Asn | Leu | Thr | Gly | Leu | Gln | Glu | Asp | Leu | Arg | Asn | Ala | Gln | Ser | Gln | Asn |
|     | 75  |     |     |     |     | 80  |     |     |     |     | 85  |     |     |     |     |

| TCA | AAA | CTC | TCC | CAG | AAC | CTG | AAC | AGA | CTC | CAA | GAC | GAT | CTA | GTC | AAC |
|-----|-----|-----|-----|-----|-----|-----|-----|-----|-----|-----|-----|-----|-----|-----|-----|
| Ser | Lys | Leu | Ser | Gln | Asn | Leu | Asn | Arg | Leu | Gln | Asp | Asp | Leu | Val | Asn |
| 90  |     |     |     |     | 95  |     |     |     |     | 100 |     |     |     |     | 105 |

| ATC | AAA | TCC | CTG | GGC | TTG | AAT | GAG | AAG | CGC | ACA | GCC | TCC | GAT | TCT | CTA |
|-----|-----|-----|-----|-----|-----|-----|-----|-----|-----|-----|-----|-----|-----|-----|-----|
| Ile | Lys | Ser | Leu | Gly | Leu | Asn | Glu | Lys | Arg | Thr | Ala | Ser | Asp | Ser | Leu |
|     |     |     |     | 110 |     |     |     |     | 115 |     |     |     |     | 120 |     |

| GAG | AAA | CTC | CAG | GAA | GAG | GTG | GCA | AAG | CTG | TGG | ATA | GAG | ATA | CTG | ATT |
|-----|-----|-----|-----|-----|-----|-----|-----|-----|-----|-----|-----|-----|-----|-----|-----|
| Glu | Lys | Leu | Gln | Glu | Glu | Val | Ala | Lys | Leu | Trp | Ile | Glu | Ile | Leu | Ile |
|     |     |     | 125 |     |     |     |     | 130 |     |     |     |     | 135 |     |     |

| TCA | AAG | GGA | ACT | GCA | TGC | AAC | ATA | TGT | CCC | AAG | AAC | TGG | CTC | CAT | TTC |
|-----|-----|-----|-----|-----|-----|-----|-----|-----|-----|-----|-----|-----|-----|-----|-----|
| Ser | Lys | Gly | Thr | Ala | Cys | Asn | Ile | Cys | Pro | Lys | Asn | Trp | Leu | His | Phe |
|     |     |     | 140 |     |     |     | 145 |     |     |     |     | 150 |     |     |     |

| CAA | CAG | AAG | TGC | TAC | TAT | TTT | GGC | AAG | GGC | TCC | AAG | CAG | TGG | ATC | CAG |
|-----|-----|-----|-----|-----|-----|-----|-----|-----|-----|-----|-----|-----|-----|-----|-----|
| Gln | Gln | Lys | Cys | Tyr | Tyr | Phe | Gly | Lys | Gly | Ser | Lys | Gln | Trp | Ile | Gln |
|     |     | 155 |     |     |     |     | 160 |     |     |     |     | 165 |     |     |     |

| GCC | AGG | TTC | GCC | TGC | AGT | GAC | CTG | CAA | GGG | CGA | CTA | GTC | AGC | ATC | CAC |
|-----|-----|-----|-----|-----|-----|-----|-----|-----|-----|-----|-----|-----|-----|-----|-----|
| Ala | Arg | Phe | Ala | Cys | Ser | Asp | Leu | Gln | Gly | Arg | Leu | Val | Ser | Ile | His |
| 170 |     |     |     |     | 175 |     |     |     |     | 180 |     |     |     |     | 185 |

Fig. 4A

```
AGC CAA AAG GAA BAG GAC TTC CTG ATG CAA CAC ATC AAC AAG AAG GAT
Ser Gln Lys Glu Gln Asp Phe Leu Met Gln His Ile Asn Lys Lys Asp
            190                 195                 200

TCC TGG ATT GGC CTC CAG GAT CTC AAT ATG GAG GGA GAG TTT GTA TGG
Ser Trp Ile Gly Leu Gln Asp Leu Asn Met Glu Gly Glu Phe Val Trp
            205                 210                 215

TCG GAC GGG AGC CCT GTG GGT TAT AGC AAC TGG AAT CCA GGG GAG CCC
Ser Asp Gly Ser Pro Val Gly Tyr Ser Asn Trp Asn Pro Gly Glu Pro
            220                 225                 230

AAT AAC GGG GGC CAG GGT GAG GAC TGT GTG ATG ATG CGG GGA TCC GGC
Asn Asn Gly Gly Gln Gly Glu Asp Cys Val Met Met Arg Gly Ser Gly
            235                 240                 245

CAG TGG AAC GAC GCC TTC TGC CGC AGC TAC TTG GAT GCA TGG GTG TGT
Gln Trp Asn Asp Ala Phe Cys Arg Ser Tyr Leu Asp Ala Trp Val Cys
250             255                 260                 265

GAG CAG CTG GCA ACA TGT GAG ATA TCT GCC CCC TTA GCC TCT GTG ACT
Glu Gln Leu Ala Thr Cys Glu Ile Ser Ala Pro Leu Ala Ser Val Thr
            270                 275                 280

CCA ACA AGG CCC ACC CCA A
Pro Thr Arg Pro Thr Pro
            285
```

Fig. 4B

```
GGAAGGATCC AAACAAGACT GCC ATG GAA GAA AAT GAA TAC TCA GCA ATG
                         Met Glu Glu Asn Glu Tyr Ser Ala Met
                          1                   5

TGG GCT GGC CTG CTG GCC CTG CTT CTT CTG TGG CAC TGG GAA ACG GAG
Trp Ala Gly Leu Leu Ala Leu Leu Leu Leu Trp His Trp Glu Thr Glu
 10              15                  20                      25

AAG AAT CTA AAA CAG CTG GGA GAC ACT GCA ATT CAG AAT GTC TCT CAT
Lys Asn Leu Lys Gln Leu Gly Asp Thr Ala Ile Gln Asn Val Ser His
                 30                  35                      40

GTT ACC AAG GAC TTA CAA AAA TTC CAG AGT AAT CAA TTG GCC CAG AAG
Val Thr Lys Asp Leu Gln Lys Phe Gln Ser Asn Gln Leu Ala Gln Lys
             45                  50                  55

TCC CAG GTT GTT CAG ATG TCA CAA AAC TTG CAA GAA CTC CAA GCT GAA
Ser Gln Val Val Gln Met Ser Gln Asn Leu Gln Glu Leu Gln Ala Glu
         60                  65                  70

CAG AAG CAA ATG AAA GCT CAG GAC TCT CGG CTC TCC CAG AAC CTG ACC
Gln Lys Gln Met Lys Ala Gln Asp Ser Arg Leu Ser Gln Asn Leu Thr
     75                  80                  85

GGA CTC CAG GAG GAT CTA AGG AAC GCC CAA TCC CAG AAC TCA AAA CTC
Gly Leu Gln Glu Asp Leu Arg Asn Ala Gln Ser Gln Asn Ser Lys Leu
 90                  95                 100                 105

TCC CAG AAC CTG AAC AGA CTC CAA GAC GAT CTA GTC AAC ATC AAA TCC
Ser Gln Asn Leu Asn Arg Leu Gln Asp Asp Leu Val Asn Ile Lys Ser
                 110                 115                 120

CTG GGC TTG AAT GAG AAG CGC ACA GCC TCC GAT TCT CTA GAG AAA CTC
Leu Gly Leu Asn Glu Lys Arg Thr Ala Ser Asp Ser Leu Glu Lys Leu
             125                 130                 135

CAG GAA GAG GTG GCA AAG CTG TGG ATA GAG ATA CTG ATT TCA AAG GGA
Gln Glu Glu Val Ala Lys Leu Trp Ile Glu Ile Leu Ile Ser Lys Gly
         140                 145                 150

ACT GCA TGC AAC ATA TGT CCC AAG AAC TGG CTC CAT TTC CAA CAG AAG
Thr Ala Cys Asn Ile Cys Pro Lys Asn Trp Leu His Phe Gln Gln Lys
     155                 160                 165

TGC TAC TAT TTT GGC AAG GGC TCC AAG CAG TGG ATC CAG GCC AGG TTC
Cys Tyr Tyr Phe Gly Lys Gly Ser Lys Gln Trp Ile Gln Ala Arg Phe
170                 175                 180                 185
```

Fig. 5A

```
GCC TGC AGT GAC CTG CAA GGG CGA CTA GTC AGC ATC CAC AGC CAA AAG
Ala Cys Ser Asp Leu Gln Gly Arg Leu Val Ser Ile His Ser Gln Lys
                190                 195                 200

GAA CAG GAC TTC CTG ATG CAA CAC ATC AAC AAG AAG GAT TCC TGG ATT
Glu Gln Asp Phe Leu Met Gln His Ile Asn Lys Lys Asp Ser Trp Ile
                205                 210                 215

GGC CTC CAG GAT CTC AAT ATG GAG GGA GAG TTT GTA TGG TCG GAC GGG
Gly Leu Gln Asp Leu Asn Met Glu Gly Glu Phe Val Trp Ser Asp Gly
            220                 225                 230

AGC CCT GTG GGT TAT AGC AAC TGG AAT CCA GGG GAG CCC AAT AAC GGG
Ser Pro Val Gly Tyr Ser Asn Trp Asn Pro Gly Glu Pro Asn Asn Gly
        235                 240                 245

GGC CAG GGT GAG GAC TGT GTG ATG ATG CGG GGA TCC GGC CAG TGG AAC
Gly Gln Gly Glu Asp Cys Val Met Met Arg Gly Ser Gly Gln Trp Asn
250                 255                 260                 265

GAC FCC TTC TGC CGC AGC TAC TTG GAT GCA TGG GTG TGT GAG CAG BTG
Asp Ala Phe Cys Arg Ser Tyr Leu Asp Ala Trp Val Cys Glu Gln Leu
                270                 275                 280

GCA ACA TGT GAG ATA TCT GCC CCC TTA GCC TCT GTG ACT CCA ACA AGG
Ala Thr Cys Glu Ile Ser Ala Pro Leu Ala Ser Val Thr Pro Thr Arg
            285                 290                 295

CCC ACC CCA A
Pro Thr Pro
        300
```

Fig. 5B

β form
```
                              GCGGGGACGCAATAGAGTCAGAGGCCAAATAGAACAGGAACTTGGAA
                              1         10        20        30        40
```

α form
```
             112       120       130       140       150       160       170
....ATTGTGCCCGCTGAGTGGACTGCGTTGTCAGGGAGTGAGTGCTCCATCATCGGGAGAAT
```

β form
```
            Met Asn Pro Pro Ser Gln|Glu Ile Glu Glu Leu Pro Arg...
CAAGCAGAATTTAGCATA ATG AAT CCT CCA AGC CAG|GAG ATC GAG GAG CTT CCC AGG...
50         60            70            80            90        100
```

α form
```
            180       190       200            210       220
CCAAGCAGGACCGCC ATG GAG GAA GGT CAA TAT TCA|GAG ATC GAG GAG CTT CCC AGG...
            Met Glu Glu Gly Gln Tyr Ser|Glu Ile Glu Glu Leu Pro Arg...
```

Fig 7

```
ATG GAG GAA GGT CAA TAT TCA GAG ATC GAG GAG CTT CCC AGG AGG CGG
Met Glu Glu Gly Gln Tyr Ser Glu Ile Glu Glu Leu Pro Arg Arg Arg
 1               5              10                 15

TGT TGC AGG CGT GGG ACT CAG ATC GTG CTG CTG GGG CTG GTG ACC GCC
Cys Bys Arg Arg Gly Thr Gln Ile Val Leu Leu Gly Leu Val Thr Ala
            20              25              30

GCT CTG TGG GCT GGC CTG CTG ACT CTG CTT CTC CTG TGG CAC TGG GAC
Ala Leu Trp Ala Gly Leu Leu Thr Leu Leu Leu Leu Trp His Trp Asp
         35              40              45

ACC ACA CAG AGT CTA AAA CAG CTG GAA GAG AGG GCT GCC CGG AAC GTC
Thr Thr Gln Ser Leu Lys Gln Leu Glu Glu Arg Ala Ala Arg Asn Val
        50              55              60

TCT CAA GTT TCC AAG AAC TTG GAA AGC CAC CAC GGT GAC CAG ATG GCG
Ser Gln Val Ser Lys Asn Leu Glu Ser His His Gly Asp Gln Met Ala
 65              70              75              80

CAG AAA TCC CAG TCC ACG CAG ATT TCA CAG GAA CTG GAG GAA CTT CGA
Gln Lys Ser Gln Ser Thr Gln Ile Ser Gln Glu Leu Glu Glu Leu Arg
                 85              90              95

GCT GAA CAG CAG AGA TTG AAA TCT CAG GAC TTG GAG CTG TCC TGG AAC
Ala Glu Gln Gln Arg Leu Lys Ser Gln Asp Leu Glu Leu Ser Trp Asn
            100             105             110

CTG AAC GGG CTT CAA GCA GAT CTG AGC AGC TTC AAG TCC BAG GAA TTG
Leu Asn Gly Leu Gln Ala Asp Leu Ser Ser Phe Lys Ser Gln Glu Leu
        115             120             125

AAC GAG AGG AAC GAA GCT TCA GAT TTG CTG GAA AGA CTC CGC GAG GAG
Asn Glu Arg Asn Glu Ala Ser Asp Leu Leu Glu Arg Leu Arg Glu Glu
    130             135             140

GTG ACA AAG CTA AGG ATG GAG TTG CAG GTC TCC AGC GGC TTT GTG TGC
Val Thr Lys Leu Arg Met Glu Leu Gln Val Ser Ser Gly Phe Val Cys
145             150             155             160

AAC ACG TGC CCT GAA AAG TGG ATC AAT TTC CAA CGC AAG TGC TAC TAC
Asn Thr Cys Pro Glu Lys Trp Ile Asn Phe Gln Arg Lys Cys Tyr Tyr
                165             170             175

TTC GGC AAG GGC ACC AAG CAG TGG GTC CAC GCC CGG TAT GCC TGT GAC
Phe Gly Lys Gly Thr Lys Gln Trp Val His Ala Arg Tyr Ala Cys Asp
            180             185             190
```

Fig. 10A

```
GAC ATG GAA GGG CAG CTG GTC AGC ATC CAC AGC CCG GAG
Asp Met Glu Gly Gln Leu Val Ser Ile His Ser Pro Glu
        195                 200             205
```

Fig. 10B

```
ATG AAT CCT CCA AGC CAG GAG ATC GAG GAG CTT CCC AGG AGG CGG TGT
Met Asn Pro Pro Ser Gln Glu Ile Glu Glu Leu Pro Arg Arg Arg Cys
 1            5                  10                 15

TGC AGG CGT GGG ACT CAG ATC GTG CTG CTG GGG CTG GTG ACC GCC GCT
Cys Arg Arg Gly Thr Gln Ile Val Leu Leu Gly Leu Val Thr Ala Ala
            20              25                  30

CTG TGG GCT GGC CTG CTG ACT CTG CTT CTC CTG TGG CAC TGG GAC ACC
Leu Trp Ala Gly Leu Leu Thr Leu Leu Leu Leu Trp His Trp Asp Thr
        35                  40                  45

ACA CAG AGT CTA AAA CAG CTG GAA GAG AGG GCT GCC CGG AAC GTC TCT
Thr Gln Ser Leu Lys Gln Leu Glu Glu Arg Ala Ala Arg Asn Val Ser
        50              55                  60

CAA GTT TCC AAG AAC TTG GAA AGC CAC CAC GGT GAC CAG ATG GCG CAG
Gln Val Ser Lys Asn Leu Glu Ser His His Gly Asp Gln Met Ala Gln
 65              70                  75                      80

AAA TCC CAG TCC ACG CAG ATT TCA CAG GAA CTG GAG GAA CTT CGA GCT
Lys Ser Gln Ser Thr Gln Ile Ser Gln Glu Leu Glu Glu Leu Arg Ala
                85                  90                  95

GAA CAG CAG AGA TTG AAA TCT CAG GAC TTG GAG CTG TCC TGG AAC CTG
Glu Gln Gln Arg Leu Lys Ser Gln Asp Leu Glu Leu Ser Trp Asn Leu
                100                 105                 110

AAC GGG CTT CAA GCA GAT CTG AGC AGC TTC AAG TCC CAG GAA TTG AAC
Asn Gly Leu Gln Ala Asp Leu Ser Ser Phe Lys Ser Gln Glu Leu Asn
            115                 120                 125

GAG AGG AAC GAA GCT TCA GAT TTG CTG GAA AGA CTC CGC GAG GAG GTG
Glu Arg Asn Glu Ala Ser Asp Leu Leu Glu Arg Leu Arg Glu Glu Val
        130                 135                 140

ACA AAG CTA AGG ATG GAG TTG CAG GTC TCC AGC GGC TTT GTG TGC AAC
Thr Lys Leu Arg Met Glu Leu Gln Val Ser Ser Gly Phe Val Cys Asn
145                 150                 155                 160

ACG TGC CCT GAA AAG TGG ATC AAT TTC CAA CGC AAG TGC TAC TAC TTC
Thr Cys Pro Glu Lys Trp Ile Asn Phe Gln Arg Lys Cys Tyr Tyr Phe
                165                 170                 175

GGC AAG GGC ACC AAG CAG TGG GTC CAC GCC CGG TAT GCC TGT GAC GAC
Gly Lys Gly Thr Lys Gln Trp Val His Ala Arg Tyr Ala Cys Asp Asp
            180                 185                 190
```

Fig. 11A

```
ATG GAA GGG CAG CTG GTC AGC ATC CAC AGC CCG GAG
Met Glu Gly Gln Leu Val Ser Ile His Ser Pro Glu
        195                 200
```

ATG GAG GAA GGT CAA TAT TCA↕ GAC TGG GAC ACC ACA CAG AGT CTA AAA
Met Glu Glu Fly Gln Tyr Ser↕ Asp Trp Asp Thr Thr Gln Ser Leu Lys
 1           5              10                      15

CAG CTG GAA GAG AGG GCT GCC CGG AAC GTC TCT CAA GTT TCC AAG AAC
Gln Leu Glu Glu Arg Ala Ala Arg Asn Val Ser Gln Val Ser Lys Asn
            20              25              30

TTG GAA AGC CAC CAC GGT GAC CAG ATG GCG CAG ⓔAA TCC CAG TCC ACG
Leu Glu Ser His His Gly Asp Gln Met Ala Gln Lys Ser Gln Ser Thr
        35              40              45

CAG ATT TCA CAG GAA CTG GAG GAA CTT CGA GCT GAA CAG CAG AGA TTG
Gln Ile Ser Gln Glu Leu Glu Glu Leu Arg Ala Glu Gln Gln Arg Leu
     50              55              60

AAA TCT CAG GAC TTG GAG CTG TCC TGG AAC CTG AAC GGG CTT CAA GCA
Lys Ser Gln Asp Leu Glu Leu Ser Trp Asn Leu Asn Gly Leu Gln Ala
 65              70              75              80

GAT CTG AGC AGC TTC AAG TCC CAG GAA TTG AAC GAG AGG AAC GAA GCT
Asp Leu Ser Ser Phe Lys Ser Gln Glu Leu Asn Glu Arg Asn Glu Ala
                85              90              95

TCA GAT TTG CTG GAA AGA CTC CGC GAG GAG GTG ACA AAG CTA AGG ATG
Ser Asp Leu Leu Glu Arg Leu Arg Glu Glu Val Thr Lys Leu Arg Met
            100             105             110

GAG TTG CAG GTC TCC AGC GGC TTT GTG TGC AAC ACG TGC CCT GAA AAG
Glu Leu Gln Val Ser Ser Gly Phe Val Cys Asn Thr Cys Pro Glu Lys
        115             120             125

TGG ATC AAT TTC CAA CGC AAG TGC TAC TAC TTC GGC AAG GGC ACC AAG
Trp Ile Asn Phe Gln Arg Lys Cys Tyr Tyr Phe Gly Lys Gly Thr Lys
    130             135             140

CAG TGG GTC CAC GCC CGG TAT GCC TGT GAC GAC ATG GAA GGG CAG CTG
Gln Trp Val His Ala Arg Tyr Ala Cys Asp Asp Met Glu Gly Gln Leu
145             150             155             160

GTC AGC ATC CAC AGC CCG GAG
Val Ser Ile His Ser Pro Glu
            165

*Fig. 12*

```
ATG AAT CCT CCA AGC CAG  GAC TGG GAC ACC ACA CAG AGT CTA AAA CAG
Met Asn Pro Pro Ser Gln  Asp Trp Asp Thr Thr Gln Ser Leu Lys Gln
 1               5                       10                  15

CTG GAA GAG AGG GCT GCC CGG AAC GTC TCT CAA GTT TCC AAG AAC TTG
Leu Glu Glu Arg Ala Ala Arg Asn Val Ser Gln Val Ser Lys Asn Leu
              20                  25                  30

GAA AGC CAC CAC GGT GAC CAG ATG GCG CAG AAA TCC CAG TCC ACG CAG
Glt Ser His His Gly Asp Gln Met Ala Gln Lys Ser Gln Ser Thr Gln
          35                  40                  45

@TT TCA CAG GAA CTG GAG GAA CTT CGA GCT GAA CAG CAG AGA TTG AAA
Ile Ser Gln Glu Leu Glu Glu Leu Arg Ala Glu Gln Gln Arg Leu Lys
      50                  55                  60

TCT CAG GAC TTG GAG CTG TCC TGG AAC CTG AAC GGG CTT CAA GCA GAT
Ser Fln Asp Leu Glu Leu Ser Trp Asn Leu Asn Gly Leu Gln Ala Asp
 65                  70                  75                  80

CTG AGC AGC TTC AAG TCC CAG GAA TTG AAC GAG AGG AAC GAA GCT TCA
Leu Ser Ser Phe Lys Ser Gln Glu Leu Asn Glu Arg Asn Glu Ala Ser
                  85                  90                  95

GAT TTG CTG GAA AGA CTC CGC GAG GAG GTG ACA AAG CTA AGG ATG GAG
Asp Leu Leu Glu Arg Leu Arg Glu Glu Val Thr Lys Leu Arg Met Glu
              100                 105                 110

TTG CAG GTC TCC AGC GGC TTT GTG TGC AAC ACG TGC CCT GAA AAG TGG
Leu Gln Val Ser Ser Gly Phe Val Cys Asn Thr Cys Pro Glu Lys Trp
          115                 120                 125

ATC AAT TTC CAA CGC AAG TGC TAC TAC TTC GGC AAG GGC ACC AAG CAG
Ile Asn Phe Gln Arg Lys Cys Tyr Tyr Phe Gly Lys Gly Thr Lys Gln
      130                 135                 140

TGG GTC CAC GCC CGG TAT GCC TGT GAC GAC ATG GAA GGG CAG CTG GTC
Trp Val His Ala Arg Tyr Ala Cys Asp Asp Met Glu Gly Gln Leu Val
145                 150                 155                 160

AGC ATC CAC AGC CCG GAG
Ser Ile His Ser Pro Glu
              165
```

Fig. 13

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
        ( A ) LENGTH: 1005 base pairs
        ( B ) TYPE: nucleic acid ( C ) STRANDEDNESS: single
( D ) TOPOLOGY: linear ( i i ) MOLECULE TYPE: cDNA ( i i i ) HYPOTHETICAL: NO ( i v ) ANTI-SENSE: NO ( i x ) FEATURE:
  ( A ) NAME/KEY: CDS
  ( B ) LOCATION: 24..1004

( x i ) SEQUENCE DESCRIPTION: SEQ ID NO:1:

```
GGAAGGATCC  AAACAAGACT  GCC ATG GAA GAA AAT GAA TAC TCA GGA TAC              50
                            Met Glu Glu Asn Glu Tyr Ser Gly Tyr
                             1                   5

TGG GAA CCT CCT AGA AAG CGT TGC TGC TGT GCA AGA CGT GGG ACA CAG              98
Trp Glu Pro Pro Arg Lys Arg Cys Cys Cys Ala Arg Arg Gly Thr Gln
 10              15                  20                      25

CTC ATG TTG GTG GGG CTG CTG AGC ACA GCA ATG TGG GCT GGC CTG CTG             146
Leu Met Leu Val Gly Leu Leu Ser Thr Ala Met Trp Ala Gly Leu Leu
                 30              35                  40

GCC CTG CTT CTT CTG TGG CAC TGG GAA ACG GAG AAG AAT CTA AAA CAG             194
Ala Leu Leu Leu Leu Trp His Trp Glu Thr Glu Lys Asn Leu Lys Gln
             45                  50                  55

CTG GGA GAC ACT GCA ATT CAG AAT GTC TCT CAT GTT ACC AAG GAC TTA             242
Leu Gly Asp Thr Ala Ile Gln Asn Val Ser His Val Thr Lys Asp Leu
         60                  65                  70

CAA AAA TTC CAG AGT AAT CAA TTG GCC CAG AAG TCC CAG GTT GTT CAG             290
Gln Lys Phe Gln Ser Asn Gln Leu Ala Gln Lys Ser Gln Val Val Gln
     75                  80                  85

ATG TCA CAA AAC TTG CAA GAA CTC CAA GCT GAA CAG AAG CAA ATG AAA             338
Met Ser Gln Asn Leu Gln Glu Leu Gln Ala Glu Gln Lys Gln Met Lys
 90                  95                 100                 105

GCT CAG GAC TCT CGG CTC TCC CAG AAC CTG ACC GGA CTC CAG GAG GAT             386
Ala Gln Asp Ser Arg Leu Ser Gln Asn Leu Thr Gly Leu Gln Glu Asp
                 110                 115                 120

CTA AGG AAC GCC CAA TCC CAG AAC TCA AAA CTC TCC CAG AAC CTG AAC             434
Leu Arg Asn Ala Gln Ser Gln Asn Ser Lys Leu Ser Gln Asn Leu Asn
             125                 130                 135

AGA CTC CAA GAC GAT CTA GTC AAC ATC AAA TCC CTG GGC TTG AAT GAG             482
Arg Leu Gln Asp Asp Leu Val Asn Ile Lys Ser Leu Gly Leu Asn Glu
         140                 145                 150

AAG CGC ACA GCC TCC GAT TCT CTA GAG AAA CTC CAG GAA GAG GTG GCA             530
Lys Arg Thr Ala Ser Asp Ser Leu Glu Lys Leu Gln Glu Glu Val Ala
     155                 160                 165

AAG CTG TGG ATA GAG ATA CTG ATT TCA AAG GGA ACT GCA TGC AAC ATA             578
Lys Leu Trp Ile Glu Ile Leu Ile Ser Lys Gly Thr Ala Cys Asn Ile
170                 175                 180                 185

TGT CCC AAG AAC TGG CTC CAT TTC CAA CAG AAG TGC TAC TAT TTT GGC             626
Cys Pro Lys Asn Trp Leu His Phe Gln Gln Lys Cys Tyr Tyr Phe Gly
                 190                 195                 200

AAG GGC TCC AAG CAG TGG ATC CAG GCC AGG TTC GCC TGC AGT GAC CTG             674
Lys Gly Ser Lys Gln Trp Ile Gln Ala Arg Phe Ala Cys Ser Asp Leu
             205                 210                 215

CAA GGG CGA CTA GTC AGC ATC CAC AGC CAA AAG GAA CAG GAC TTC CTG             722
Gln Gly Arg Leu Val Ser Ile His Ser Gln Lys Glu Gln Asp Phe Leu
         220                 225                 230

ATG CAA CAC ATC AAC AAG AAG GAT TCC TGG ATT GGC CTC CAG GAT CTC             770
Met Gln His Ile Asn Lys Lys Asp Ser Trp Ile Gly Leu Gln Asp Leu
     235                 240                 245

AAT ATG GAG GGA GAG TTT GTA TGG TCG GAC GGG AGC CCT GTG GGT TAT             818
```

| Asn | Met | Glu | Gly | Glu | Phe | Val | Trp | Ser | Asp | Gly | Ser | Pro | Val | Gly | Tyr | |
|---|---|---|---|---|---|---|---|---|---|---|---|---|---|---|---|---|
| 250 | | | | 255 | | | | | 260 | | | | | 265 | | |

| AGC | AAC | TGG | AAT | CCA | GGG | GAG | CCC | AAT | AAC | GGG | GGC | CAG | GGT | GAG | GAC | 866 |
|---|---|---|---|---|---|---|---|---|---|---|---|---|---|---|---|---|
| Ser | Asn | Trp | Asn | Pro | Gly | Glu | Pro | Asn | Asn | Gly | Gly | Gln | Gly | Glu | Asp | |
| | | | | 270 | | | | | 275 | | | | | 280 | | |

| TGT | GTG | ATG | ATG | CGG | GGA | TCC | GGC | CAG | TGG | AAC | GAC | GCC | TTC | TGC | CGC | 914 |
|---|---|---|---|---|---|---|---|---|---|---|---|---|---|---|---|---|
| Cys | Val | Met | Met | Arg | Gly | Ser | Gly | Gln | Trp | Asn | Asp | Ala | Phe | Cys | Arg | |
| | | | 285 | | | | | 290 | | | | | 295 | | | |

| AGC | TAC | TTG | GAT | GCA | TGG | GTG | TGT | GAG | CAG | CTG | GCA | ACA | TGT | GAG | ATA | 962 |
|---|---|---|---|---|---|---|---|---|---|---|---|---|---|---|---|---|
| Ser | Tyr | Leu | Asp | Ala | Trp | Val | Cys | Glu | Gln | Leu | Ala | Thr | Cys | Glu | Ile | |
| | | | 300 | | | | | 305 | | | | | 310 | | | |

| TCT | GCC | CCC | TTA | GCC | TCT | GTG | ACT | CCA | ACA | AGG | CCC | ACC | CCA | A | | 1005 |
|---|---|---|---|---|---|---|---|---|---|---|---|---|---|---|---|---|
| Ser | Ala | Pro | Leu | Ala | Ser | Val | Thr | Pro | Thr | Arg | Pro | Thr | Pro | | | |
| | 315 | | | | | 320 | | | | | 325 | | | | | |

(2) INFORMATION FOR SEQ ID NO:2:

(i) SEQUENCE CHARACTERISTICS:
        (A) LENGTH: 327 amino acids
        (B) TYPE: amino acid
        (D) TOPOLOGY: linear (ii) MOLECULE TYPE: protein (xi) SEQUENCE DESCRIPTION: SEQ ID NO:2:

| Met | Glu | Glu | Asn | Glu | Tyr | Ser | Gly | Tyr | Trp | Glu | Pro | Pro | Arg | Lys | Arg |
|---|---|---|---|---|---|---|---|---|---|---|---|---|---|---|---|
| 1 | | | | 5 | | | | | 10 | | | | | 15 | |

| Cys | Cys | Cys | Ala | Arg | Arg | Gly | Thr | Gln | Leu | Met | Leu | Val | Gly | Leu | Leu |
|---|---|---|---|---|---|---|---|---|---|---|---|---|---|---|---|
| | | | 20 | | | | | 25 | | | | | 30 | | |

| Ser | Thr | Ala | Met | Trp | Ala | Gly | Leu | Leu | Ala | Leu | Leu | Leu | Leu | Trp | His |
|---|---|---|---|---|---|---|---|---|---|---|---|---|---|---|---|
| | | | 35 | | | | | 40 | | | | | 45 | | |

| Trp | Glu | Thr | Glu | Lys | Asn | Leu | Lys | Gln | Leu | Gly | Asp | Thr | Ala | Ile | Gln |
|---|---|---|---|---|---|---|---|---|---|---|---|---|---|---|---|
| | 50 | | | | | 55 | | | | | 60 | | | | |

| Asn | Val | Ser | His | Val | Thr | Lys | Asp | Leu | Gln | Lys | Phe | Gln | Ser | Asn | Gln |
|---|---|---|---|---|---|---|---|---|---|---|---|---|---|---|---|
| 65 | | | | | 70 | | | | | 75 | | | | | 80 |

| Leu | Ala | Gln | Lys | Ser | Gln | Val | Val | Gln | Met | Ser | Gln | Asn | Leu | Gln | Glu |
|---|---|---|---|---|---|---|---|---|---|---|---|---|---|---|---|
| | | | | 85 | | | | | 90 | | | | | 95 | |

| Leu | Gln | Ala | Glu | Gln | Lys | Gln | Met | Lys | Ala | Gln | Asp | Ser | Arg | Leu | Ser |
|---|---|---|---|---|---|---|---|---|---|---|---|---|---|---|---|
| | | | | 100 | | | | | 105 | | | | | 110 | |

| Gln | Asn | Leu | Thr | Gly | Leu | Gln | Glu | Asp | Leu | Arg | Asn | Ala | Gln | Ser | Gln |
|---|---|---|---|---|---|---|---|---|---|---|---|---|---|---|---|
| | | | 115 | | | | | 120 | | | | | 125 | | |

| Asn | Ser | Lys | Leu | Ser | Gln | Asn | Leu | Asn | Arg | Leu | Gln | Asp | Asp | Leu | Val |
|---|---|---|---|---|---|---|---|---|---|---|---|---|---|---|---|
| | 130 | | | | | 135 | | | | | 140 | | | | |

| Asn | Ile | Lys | Ser | Leu | Gly | Leu | Asn | Glu | Lys | Arg | Thr | Ala | Ser | Asp | Ser |
|---|---|---|---|---|---|---|---|---|---|---|---|---|---|---|---|
| 145 | | | | | 150 | | | | | 155 | | | | | 160 |

| Leu | Glu | Lys | Leu | Gln | Glu | Glu | Val | Ala | Lys | Leu | Trp | Ile | Glu | Ile | Leu |
|---|---|---|---|---|---|---|---|---|---|---|---|---|---|---|---|
| | | | | 165 | | | | | 170 | | | | | 175 | |

| Ile | Ser | Lys | Gly | Thr | Ala | Cys | Asn | Ile | Cys | Pro | Lys | Asn | Trp | Leu | His |
|---|---|---|---|---|---|---|---|---|---|---|---|---|---|---|---|
| | | | 180 | | | | | 185 | | | | | 190 | | |

| Phe | Gln | Gln | Lys | Cys | Tyr | Tyr | Phe | Gly | Lys | Gly | Ser | Lys | Gln | Trp | Ile |
|---|---|---|---|---|---|---|---|---|---|---|---|---|---|---|---|
| | | 195 | | | | | 200 | | | | | 205 | | | |

| Gln | Ala | Arg | Phe | Ala | Cys | Ser | Asp | Leu | Gln | Gly | Arg | Leu | Val | Ser | Ile |
|---|---|---|---|---|---|---|---|---|---|---|---|---|---|---|---|
| | 210 | | | | | 215 | | | | | 220 | | | | |

| His | Ser | Gln | Lys | Glu | Gln | Asp | Phe | Leu | Met | Gln | His | Ile | Asn | Lys | Lys |
|---|---|---|---|---|---|---|---|---|---|---|---|---|---|---|---|
| 225 | | | | | 230 | | | | | 235 | | | | | 240 |

| Asp | Ser | Trp | Ile | Gly | Leu | Gln | Asp | Leu | Asn | Met | Glu | Gly | Glu | Phe | Val |
|---|---|---|---|---|---|---|---|---|---|---|---|---|---|---|---|
| | | | | 245 | | | | | 250 | | | | | 255 | |

| Trp | Ser | Asp | Gly | Ser | Pro | Val | Gly | Tyr | Ser | Asn | Trp | Asn | Pro | Gly | Glu |
|---|---|---|---|---|---|---|---|---|---|---|---|---|---|---|---|

|  | 260 |  |  |  | 265 |  |  |  |  | 270 |  |  |
|---|---|---|---|---|---|---|---|---|---|---|---|---|

Pro Asn Asn Gly Gly Gln Gly Glu Asp Cys Val Met Met Arg Gly Ser
     275                      280                 285

Gly Gln Trp Asn Asp Ala Phe Cys Arg Ser Tyr Leu Asp Ala Trp Val
290                       295                     300

Cys Glu Gln Leu Ala Thr Cys Glu Ile Ser Ala Pro Leu Ala Ser Val
305                  310                  315                 320

Thr Pro Thr Arg Pro Thr Pro
               325

( 2 ) INFORMATION FOR SEQ ID NO:3:

( i ) SEQUENCE CHARACTERISTICS:
        ( A ) LENGTH: 885 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 24..884

( x i ) SEQUENCE DESCRIPTION: SEQ ID NO:3:

```
GGAAGGATCC  AAACAAGACT  GCC ATG GAA GAA AAT GAA TAC TCA GAC TGG         50
                            Met Glu Glu Asn Glu Tyr Ser Asp Trp
                             1               5

GAA ACG GAG AAG AAT CTA AAA CAG CTG GGA GAC ACT GCA ATT CAG AAT         98
Glu Thr Glu Lys Asn Leu Lys Gln Leu Gly Asp Thr Ala Ile Gln Asn
 10              15                  20                  25

GTC TCT CAT GTT ACC AAG GAC TTA CAA AAA TTC CAG AGT AAT CAA TTG        146
Val Ser His Val Thr Lys Asp Leu Gln Lys Phe Gln Ser Asn Gln Leu
                 30                  35                  40

GCC CAG AAG TCC CAG GTT GTT CAG ATG TCA CAA AAC TTG CAA GAA CTC        194
Ala Gln Lys Ser Gln Val Val Gln Met Ser Gln Asn Leu Gln Glu Leu
             45                  50                  55

CAA GCT GAA CAG AAG CAA ATG AAA GCT CAG GAC TCT CGG CTC TCC CAG        242
Gln Ala Glu Gln Lys Gln Met Lys Ala Gln Asp Ser Arg Leu Ser Gln
         60                  65                  70

AAC CTG ACC GGA CTC CAG GAG GAT CTA AGG AAC GCC CAA TCC CAG AAC        290
Asn Leu Thr Gly Leu Gln Glu Asp Leu Arg Asn Ala Gln Ser Gln Asn
     75                  80                  85

TCA AAA CTC TCC CAG AAC CTG AAC AGA CTC CAA GAC GAT CTA GTC AAC        338
Ser Lys Leu Ser Gln Asn Leu Asn Arg Leu Gln Asp Asp Leu Val Asn
 90                  95                 100                 105

ATC AAA TCC CTG GGC TTG AAT GAG AAG CGC ACA GCC TCC GAT TCT CTA        386
Ile Lys Ser Leu Gly Leu Asn Glu Lys Arg Thr Ala Ser Asp Ser Leu
                110                 115                 120

GAG AAA CTC CAG GAA GAG GTG GCA AAG CTG TGG ATA GAG ATA CTG ATT        434
Glu Lys Leu Gln Glu Glu Val Ala Lys Leu Trp Ile Glu Ile Leu Ile
            125                 130                 135

TCA AAG GGA ACT GCA TGC AAC ATA TGT CCC AAG AAC TGG CTC CAT TTC        482
Ser Lys Gly Thr Ala Cys Asn Ile Cys Pro Lys Asn Trp Leu His Phe
        140                 145                 150

CAA CAG AAG TGC TAC TAT TTT GGC AAG GGC TCC AAG CAG TGG ATC CAG        530
Gln Gln Lys Cys Tyr Tyr Phe Gly Lys Gly Ser Lys Gln Trp Ile Gln
    155                 160                 165

GCC AGG TTC GCC TGC AGT GAC CTG CAA GGG CGA CTA GTC AGC ATC CAC        578
```

|  |  |  |  |  |  |  |  |  |  |  |  |  |  |  |  |
|---|---|---|---|---|---|---|---|---|---|---|---|---|---|---|---|
| Ala | Arg | Phe | Ala | Cys | Ser | Asp | Leu | Gln | Gly | Arg | Leu | Val | Ser | Ile | His |
| 170 |  |  |  | 175 |  |  |  |  | 180 |  |  |  |  | 185 |  |

| AGC | CAA | AAG | GAA | CAG | GAC | TTC | CTG | ATG | CAA | CAC | ATC | AAC | AAG | AAG | GAT | 626 |
|---|---|---|---|---|---|---|---|---|---|---|---|---|---|---|---|---|
| Ser | Gln | Lys | Glu | Gln | Asp | Phe | Leu | Met | Gln | His | Ile | Asn | Lys | Lys | Asp |  |
|  |  |  |  | 190 |  |  |  |  | 195 |  |  |  |  | 200 |  |  |

| TCC | TGG | ATT | GGC | CTC | CAG | GAT | CTC | AAT | ATG | GAG | GGA | GAG | TTT | GTA | TGG | 674 |
|---|---|---|---|---|---|---|---|---|---|---|---|---|---|---|---|---|
| Ser | Trp | Ile | Gly | Leu | Gln | Asp | Leu | Asn | Met | Glu | Gly | Glu | Phe | Val | Trp |  |
|  |  |  | 205 |  |  |  |  |  | 210 |  |  |  |  | 215 |  |  |

| TCG | GAC | GGG | AGC | CCT | GTG | GGT | TAT | AGC | AAC | TGG | AAT | CCA | GGG | GAG | CCC | 722 |
|---|---|---|---|---|---|---|---|---|---|---|---|---|---|---|---|---|
| Ser | Asp | Gly | Ser | Pro | Val | Gly | Tyr | Ser | Asn | Trp | Asn | Pro | Gly | Glu | Pro |  |
|  |  | 220 |  |  |  |  | 225 |  |  |  |  | 230 |  |  |  |  |

| AAT | AAC | GGG | GGC | CAG | GGT | GAG | GAC | TGT | GTG | ATG | ATG | CGG | GGA | TCC | GGC | 770 |
|---|---|---|---|---|---|---|---|---|---|---|---|---|---|---|---|---|
| Asn | Asn | Gly | Gly | Gln | Gly | Glu | Asp | Cys | Val | Met | Met | Arg | Gly | Ser | Gly |  |
|  | 235 |  |  |  |  | 240 |  |  |  |  | 245 |  |  |  |  |  |

| CAG | TGG | AAC | GAC | GCC | TTC | TGC | CGC | AGC | TAC | TTG | GAT | GCA | TGG | GTG | TGT | 818 |
|---|---|---|---|---|---|---|---|---|---|---|---|---|---|---|---|---|
| Gln | Trp | Asn | Asp | Ala | Phe | Cys | Arg | Rer | Tyr | Leu | Asp | Ala | Trp | Val | Cys |  |
| 250 |  |  |  |  | 255 |  |  |  |  | 260 |  |  |  |  | 265 |  |

| GAG | BAG | CTG | GCA | ACA | TGT | GAG | ATA | TCT | GCC | CCC | TTA | GCC | TCT | GTG | ACT | 866 |
|---|---|---|---|---|---|---|---|---|---|---|---|---|---|---|---|---|
| Glu | Gln | Leu | Ala | Thr | Cys | Glu | Ile | Ser | Ala | Pro | Leu | Ala | Ser | Val | Thr |  |
|  |  |  |  | 270 |  |  |  |  | 275 |  |  |  |  | 280 |  |  |

| CCA | ACA | AGG | CCC | ACC | CCA | A |  |  |  |  |  |  |  |  |  | 885 |
|---|---|---|---|---|---|---|---|---|---|---|---|---|---|---|---|---|
| Pro | Thr | Arg | Pro | Thr | Pro |  |  |  |  |  |  |  |  |  |  |  |
|  |  |  | 285 |  |  |  |  |  |  |  |  |  |  |  |  |  |

( 2 ) INFORMATION FOR SEQ ID NO:4:

( i ) SEQUENCE CHARACTERISTICS:
        ( A ) LENGTH: 287 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

|  |  |  |  |  |  |  |  |  |  |  |  |  |  |  |  |
|---|---|---|---|---|---|---|---|---|---|---|---|---|---|---|---|
| Met | Glu | Glu | Asn | Glu | Tyr | Ser | Asp | Trp | Glu | Thr | Glu | Lys | Asn | Leu | Lys |
| 1 |  |  |  | 5 |  |  |  |  | 10 |  |  |  |  | 15 |  |

| Gln | Leu | Gly | Asp | Thr | Ala | Ile | Gln | Asn | Val | Ser | His | Val | Thr | Lys | Asp |
|---|---|---|---|---|---|---|---|---|---|---|---|---|---|---|---|
|  |  |  | 20 |  |  |  |  | 25 |  |  |  |  | 30 |  |  |

| Leu | Gln | Lys | Phe | Gln | Ser | Asn | Gln | Leu | Ala | Gln | Lys | Ser | Gln | Val | Val |
|---|---|---|---|---|---|---|---|---|---|---|---|---|---|---|---|
|  |  | 35 |  |  |  |  | 40 |  |  |  |  | 45 |  |  |  |

| Gln | Met | Ser | Gln | Asn | Leu | Gln | Glu | Leu | Gln | Ala | Glu | Gln | Lys | Gln | Met |
|---|---|---|---|---|---|---|---|---|---|---|---|---|---|---|---|
|  | 50 |  |  |  |  | 55 |  |  |  |  | 60 |  |  |  |  |

| Lys | Ala | Gln | Asp | Ser | Arg | Leu | Ser | Gln | Asn | Leu | Thr | Gly | Leu | Gln | Glu |
|---|---|---|---|---|---|---|---|---|---|---|---|---|---|---|---|
| 65 |  |  |  |  | 70 |  |  |  |  | 75 |  |  |  |  | 80 |

| Asp | Leu | Arg | Asn | Ala | Gln | Ser | Gln | Asn | Ser | Lys | Leu | Ser | Gln | Asn | Leu |
|---|---|---|---|---|---|---|---|---|---|---|---|---|---|---|---|
|  |  |  |  | 85 |  |  |  |  | 90 |  |  |  |  | 95 |  |

| Asn | Arg | Leu | Gln | Asp | Asp | Leu | Val | Asn | Ile | Lys | Ser | Leu | Gly | Leu | Asn |
|---|---|---|---|---|---|---|---|---|---|---|---|---|---|---|---|
|  |  |  | 100 |  |  |  |  | 105 |  |  |  |  | 110 |  |  |

| Glu | Lys | Arg | Thr | Ala | Ser | Asp | Ser | Leu | Glu | Lys | Leu | Gln | Glu | Glu | Val |
|---|---|---|---|---|---|---|---|---|---|---|---|---|---|---|---|
|  |  | 115 |  |  |  |  | 120 |  |  |  |  | 125 |  |  |  |

| Ala | Lys | Leu | Trp | Ile | Glu | Ile | Leu | Ile | Ser | Lys | Gly | Thr | Ala | Cys | Asn |
|---|---|---|---|---|---|---|---|---|---|---|---|---|---|---|---|
|  | 130 |  |  |  |  | 135 |  |  |  |  | 140 |  |  |  |  |

| Ile | Cys | Pro | Lys | Asn | Trp | Leu | His | Phe | Gln | Gln | Lys | Cys | Tyr | Tyr | Phe |
|---|---|---|---|---|---|---|---|---|---|---|---|---|---|---|---|
| 145 |  |  |  |  | 150 |  |  |  |  | 155 |  |  |  |  | 160 |

| Gly | Lys | Gly | Ser | Lys | Gln | Trp | Ile | Gln | Ala | Arg | Phe | Ala | Cys | Ser | Asp |
|---|---|---|---|---|---|---|---|---|---|---|---|---|---|---|---|
|  |  |  | 165 |  |  |  |  | 170 |  |  |  |  | 175 |  |  |

| Leu | Gln | Gly | Arg | Leu | Val | Ser | Ile | His | Ser | Gln | Lys | Glu | Gln | Asp | Phe |
|---|---|---|---|---|---|---|---|---|---|---|---|---|---|---|---|
|  |  |  | 180 |  |  |  |  | 185 |  |  |  |  | 190 |  |  |

| Leu | Met | Gln | His | Ile | Asn | Lys | Lys | Asp | Ser | Trp | Ile | Gly | Leu | Gln | Asp |

|   | 195 |   |   |   |   | 200 |   |   |   |   | 205 |   |   |   |
|---|---|---|---|---|---|---|---|---|---|---|---|---|---|---|
| Leu | Asn | Met | Glu | Gly | Glu | Phe | Val | Trp | Ser | Asp | Gly | Ser | Pro | Val | Gly |
|   | 210 |   |   |   |   | 215 |   |   |   |   | 220 |   |   |   |   |
| Tyr | Ser | Asn | Trp | Asn | Pro | Gly | Glu | Pro | Asn | Asn | Gly | Gly | Gln | Gly | Glu |
| 225 |   |   |   |   | 230 |   |   |   |   | 235 |   |   |   |   | 240 |
| Asp | Cys | Val | Met | Met | Arg | Gly | Ser | Gly | Gln | Trp | Asn | Asp | Ala | Phe | Cys |
|   |   |   |   | 245 |   |   |   |   | 250 |   |   |   |   | 255 |   |
| Arg | Ser | Tyr | Leu | Asp | Ala | Trp | Val | Cys | Glu | Gln | Leu | Ala | Thr | Cys | Glu |
|   |   |   | 260 |   |   |   |   | 265 |   |   |   |   | 270 |   |   |
| Ile | Ser | Ala | Pro | Leu | Ala | Ser | Val | Thr | Pro | Thr | Arg | Pro | Thr | Pro |   |
|   |   | 275 |   |   |   |   | 280 |   |   |   |   | 285 |   |   |   |

( 2 ) INFORMATION FOR SEQ ID NO:5:

( i ) SEQUENCE CHARACTERISTICS:
        ( A ) LENGTH: 924 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 24..923

( x i ) SEQUENCE DESCRIPTION: SEQ ID NO:5:

| GGAAGGATCC | AAACAAGACT | GCC | ATG | GAA | GAA | AAT | GAA | TAC | TCA | GCA | ATG | 50 |
|---|---|---|---|---|---|---|---|---|---|---|---|---|
|   |   |   | Met | Glu | Glu | Asn | Glu | Tyr | Ser | Ala | Met |   |
|   |   |   | 1 |   |   |   | 5 |   |   |   |   |   |
| TGG | GCT | GGC | CTG | CTG | GCC | CTG | CTT | CTT | CTG | TGG | CAC | TGG | GAA | ACG | GAG | 98 |
| Trp | Ala | Gly | Leu | Leu | Ala | Leu | Leu | Leu | Leu | Trp | His | Trp | Glu | Thr | Glu |   |
| 10 |   |   |   |   | 15 |   |   |   |   | 20 |   |   |   |   | 25 |   |
| AAG | AAT | CTA | AAA | CAG | CTG | GGA | GAC | ACT | GCA | ATT | CAG | AAT | GTC | TCT | CAT | 146 |
| Lys | Asn | Leu | Lys | Gln | Leu | Gly | Asp | Thr | Ala | Ile | Gln | Asn | Val | Ser | His |   |
|   |   |   |   | 30 |   |   |   |   | 35 |   |   |   |   | 40 |   |   |
| GTT | ACC | AAG | GAC | TTA | CAA | AAA | TTC | CAG | AGT | AAT | CAA | TTG | GCC | CAG | AAG | 194 |
| Val | Thr | Lys | Asp | Leu | Gln | Lys | Phe | Gln | Ser | Asn | Gln | Leu | Ala | Gln | Lys |   |
|   |   |   | 45 |   |   |   |   | 50 |   |   |   |   | 55 |   |   |   |
| TCC | CAG | GTT | GTT | CAG | ATG | TCA | CAA | AAC | TTG | CAA | GAA | CTC | CAA | GCT | GAA | 242 |
| Ser | Gln | Val | Val | Gln | Met | Ser | Gln | Asn | Leu | Gln | Glu | Leu | Gln | Ala | Glu |   |
|   |   | 60 |   |   |   |   | 65 |   |   |   |   | 70 |   |   |   |   |
| CAG | AAG | CAA | ATG | AAA | GCT | CAG | GAC | TCT | CGG | CTC | TCC | CAG | AAC | CTG | ACC | 290 |
| Gln | Lys | Gln | Met | Lys | Ala | Gln | Asp | Ser | Arg | Leu | Ser | Gln | Asn | Leu | Thr |   |
|   | 75 |   |   |   |   | 80 |   |   |   |   | 85 |   |   |   |   |   |
| GGA | CTC | CAG | GAG | GAT | CTA | AGG | AAC | GCC | CAA | TCC | CAG | AAC | TCA | AAA | CTC | 338 |
| Gly | Leu | Gln | Glu | Asp | Leu | Arg | Asn | Ala | Gln | Ser | Gln | Asn | Ser | Lys | Leu |   |
| 90 |   |   |   |   | 95 |   |   |   |   | 100 |   |   |   |   | 105 |   |
| TCC | CAG | AAC | CTG | AAC | AGA | CTC | CAA | GAC | GAT | CTA | GTC | AAC | ATC | AAA | TCC | 386 |
| Ser | Gln | Asn | Leu | Asn | Arg | Leu | Gln | Asp | Asp | Leu | Val | Asn | Ile | Lys | Ser |   |
|   |   |   |   | 110 |   |   |   |   | 115 |   |   |   |   | 120 |   |   |
| CTG | GGC | TTG | AAT | GAG | AAG | CGC | ACA | GCC | TCC | GAT | TCT | CTA | GAG | AAA | CTC | 434 |
| Leu | Gly | Leu | Asn | Glu | Lys | Arg | Thr | Ala | Ser | Asp | Ser | Leu | Glu | Lys | Leu |   |
|   |   |   | 125 |   |   |   |   | 130 |   |   |   |   | 135 |   |   |   |
| CAG | GAA | GAG | GTG | GCA | AAG | CTG | TGG | ATA | GAG | ATA | CTG | ATT | TCA | AAG | GGA | 482 |
| Gln | Glu | Glu | Val | Ala | Lys | Leu | Trp | Ile | Glu | Ile | Leu | Ile | Ser | Lys | Gly |   |
|   |   | 140 |   |   |   |   | 145 |   |   |   |   | 150 |   |   |   |   |
| ACT | GCA | TGC | AAC | ATA | TGT | CCC | AAG | AAC | TGG | CTC | CAT | TTC | CAA | CAG | AAG | 530 |
| Thr | Ala | Cys | Asn | Ile | Cys | Pro | Lys | Asn | Trp | Leu | His | Phe | Gln | Gln | Lys |   |

-continued

| | | | | | | | | | | | | | | | | |
|---|---|---|---|---|---|---|---|---|---|---|---|---|---|---|---|---|
| | 155 | | | | | 160 | | | | | 165 | | | | | |
| TGC | TAC | TAT | TTT | GGC | AAG | GGC | TCC | AAG | CAG | TGG | ATC | CAG | GCC | AGG | TTC | 578 |
| Cys | Tyr | Tyr | Phe | Gly | Lys | Gly | Ser | Lys | Gln | Trp | Ile | Gln | Ala | Arg | Phe | |
| 170 | | | | 175 | | | | | 180 | | | | | | 185 | |
| GCC | TGC | AGT | GAC | CTG | CAA | GGG | CGA | CTA | GTC | AGC | ATC | CAC | AGC | CAA | AAG | 626 |
| Ala | Cys | Ser | Asp | Leu | Gln | Gly | Arg | Leu | Val | Ser | Ile | His | Ser | Gln | Lys | |
| | | | | 190 | | | | | 195 | | | | | 200 | | |
| GAA | CAG | GAC | TTC | CTG | ATG | CAA | CAC | ATC | AAC | AAG | AAG | GAT | TCC | TGG | ATT | 674 |
| Glu | Gln | Asp | Phe | Leu | Met | Gln | His | Ile | Asn | Lys | Lys | Asp | Ser | Trp | Ile | |
| | | | 205 | | | | | 210 | | | | | 215 | | | |
| GGC | CTC | CAG | GAT | CTC | AAT | ATG | GAG | GGA | GAG | TTT | GTA | TGG | TCG | GAC | GGG | 722 |
| Gly | Leu | Gln | Asp | Leu | Asn | Met | Glu | Gly | Glu | Phe | Val | Trp | Ser | Asp | Gly | |
| | | 220 | | | | | 225 | | | | | 230 | | | | |
| AGC | CCT | GTG | GGT | TAT | AGC | AAC | TGG | AAT | CCA | GGG | GAG | CCC | AAT | AAC | GGG | 770 |
| Ser | Pro | Val | Gly | Tyr | Ser | Asn | Trp | Asn | Pro | Gly | Glu | Pro | Asn | Asn | Gly | |
| | 235 | | | | | 240 | | | | | 245 | | | | | |
| GGC | CAG | GGT | GAG | GAC | TGT | GTG | ATG | ATG | CGG | GGA | TCC | GGC | CAG | TGG | AAC | 818 |
| Gly | Gln | Gly | Glu | Asp | Cys | Val | Met | Met | Arg | Gly | Ser | Gly | Gln | Trp | Asn | |
| 250 | | | | | 255 | | | | | 260 | | | | | 265 | |
| GAC | GCC | TTC | TGC | CGC | AGC | TAC | TTG | GAT | GCA | TGG | GTG | TGT | GAG | CAG | CTG | 866 |
| Asp | Ala | Phe | Cys | Arg | Ser | Tyr | Leu | Asp | Ala | Trp | Val | Cys | Glu | Gln | Leu | |
| | | | | 270 | | | | | 275 | | | | | 280 | | |
| GCA | ACA | TGT | GAG | ATA | TCT | GCC | CCC | TTA | GCC | TCT | GTG | ACT | CCA | ACA | AGG | 914 |
| Ala | Thr | Cys | Glu | Ile | Ser | Ala | Pro | Leu | Ala | Ser | Val | Thr | Pro | Thr | Arg | |
| | | | 285 | | | | | 290 | | | | | 295 | | | |
| CCC | ACC | CCA | A | | | | | | | | | | | | | 924 |
| Pro | Thr | Pro | | | | | | | | | | | | | | |
| | | 300 | | | | | | | | | | | | | | |

( 2 ) INFORMATION FOR SEQ ID NO:6:

( i ) SEQUENCE CHARACTERISTICS:
        ( A ) LENGTH: 300 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

| Met | Glu | Glu | Asn | Glu | Tyr | Ser | Ala | Met | Trp | Ala | Gly | Leu | Leu | Ala | Leu |
|---|---|---|---|---|---|---|---|---|---|---|---|---|---|---|---|
| 1 | | | | 5 | | | | | 10 | | | | | 15 | |

| Leu | Leu | Leu | Trp | His | Trp | Glu | Thr | Glu | Lys | Asn | Leu | Lys | Gln | Leu | Gly |
|---|---|---|---|---|---|---|---|---|---|---|---|---|---|---|---|
| | | | 20 | | | | | 25 | | | | | 30 | | |

| Asp | Thr | Ala | Ile | Gln | Asn | Val | Ser | His | Val | Thr | Lys | Asp | Leu | Gln | Lys |
|---|---|---|---|---|---|---|---|---|---|---|---|---|---|---|---|
| | | 35 | | | | | 40 | | | | | 45 | | | |

| Phe | Gln | Ser | Asn | Gln | Leu | Ala | Gln | Lys | Ser | Gln | Val | Val | Gln | Met | Ser |
|---|---|---|---|---|---|---|---|---|---|---|---|---|---|---|---|
| | 50 | | | | | 55 | | | | | 60 | | | | |

| Gln | Asn | Leu | Gln | Glu | Leu | Gln | Ala | Glu | Gln | Lys | Gln | Met | Lys | Ala | Gln |
|---|---|---|---|---|---|---|---|---|---|---|---|---|---|---|---|
| 65 | | | | | 70 | | | | | 75 | | | | | 80 |

| Asp | Ser | Arg | Leu | Ser | Gln | Asn | Leu | Thr | Gly | Leu | Gln | Glu | Asp | Leu | Arg |
|---|---|---|---|---|---|---|---|---|---|---|---|---|---|---|---|
| | | | | 85 | | | | | 90 | | | | | 95 | |

| Asn | Ala | Gln | Ser | Gln | Asn | Ser | Lys | Leu | Ser | Gln | Asn | Leu | Asn | Arg | Leu |
|---|---|---|---|---|---|---|---|---|---|---|---|---|---|---|---|
| | | | 100 | | | | | 105 | | | | | 110 | | |

| Gln | Asp | Asp | Leu | Val | Asn | Ile | Lys | Ser | Leu | Gly | Leu | Asn | Glu | Lys | Arg |
|---|---|---|---|---|---|---|---|---|---|---|---|---|---|---|---|
| | | 115 | | | | | 120 | | | | | 125 | | | |

| Thr | Ala | Ser | Asp | Ser | Leu | Glu | Lys | Leu | Gln | Glu | Glu | Val | Ala | Lys | Leu |
|---|---|---|---|---|---|---|---|---|---|---|---|---|---|---|---|
| | 130 | | | | | 135 | | | | | 140 | | | | |

| Trp | Ile | Glu | Ile | Leu | Ile | Ser | Lys | Gly | Thr | Ala | Cys | Asn | Ile | Cys | Pro |
|---|---|---|---|---|---|---|---|---|---|---|---|---|---|---|---|
| 145 | | | | | 150 | | | | | 155 | | | | | 160 |

```
Lys Asn Trp Leu His Phe Gln Gln Lys Cys Tyr Tyr Phe Gly Lys Gly
            165                 170                 175

Ser Lys Gln Trp Ile Gln Ala Arg Phe Ala Cys Ser Asp Leu Gln Gly
            180                 185                 190

Arg Leu Val Ser Ile His Ser Gln Lys Glu Gln Asp Phe Leu Met Gln
            195                 200                 205

His Ile Asn Lys Lys Asp Ser Trp Ile Gly Leu Gln Asp Leu Asn Met
    210                 215                 220

Glu Gly Glu Phe Val Trp Ser Asp Gly Ser Pro Val Gly Tyr Ser Asn
225                 230                 235                 240

Trp Asn Pro Gly Glu Pro Asn Asn Gly Gly Gln Gly Glu Asp Cys Val
            245                 250                 255

Met Met Arg Gly Ser Gly Gln Trp Asn Asp Ala Phe Cys Arg Ser Tyr
            260                 265                 270

Leu Asp Ala Trp Val Cys Glu Gln Leu Ala Thr Cys Glu Ile Ser Ala
            275                 280                 285

Pro Leu Ala Ser Val Thr Pro Thr Arg Pro Thr Pro
            290                 295                 300
```

( 2 ) INFORMATION FOR SEQ ID NO:7:

( i ) SEQUENCE CHARACTERISTICS:
        ( A ) LENGTH: 1037 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 75..1037

( x i ) SEQUENCE DESCRIPTION: SEQ ID NO:7:

```
ATTGTGCCCG CTGAGTGGAC TGCGTTGTCA GGGAGTGAGT GCTCCATCAT CGGGAGAATC        60

CAAGCAGGAC CGCC ATG GAG GAA GGT CAA TAT TCA GAG ATC GAG GAG CTT        110
              Met Glu Glu Gly Gln Tyr Ser Glu Ile Glu Glu Leu
               1               5                  10

CCC AGG AGG CGG TGT TGC AGG CGT GGG ACT CAG ATC GTG CTG CTG GGG        158
Pro Arg Arg Arg Cys Cys Arg Arg Gly Thr Gln Ile Val Leu Leu Gly
         15                  20                  25

CTG GTG ACC GCC GCT CTG TGG GCT GGC CTG CTG ACT CTG CTT CTC CTG        206
Leu Val Thr Ala Ala Leu Trp Ala Gly Leu Leu Thr Leu Leu Leu Leu
         30                  35                  40

TGG CAC TGG GAC ACC ACA CAG AGT CTA AAA CAG CTG GAA GAG AGG GCT        254
Trp His Trp Asp Thr Thr Gln Ser Leu Lys Gln Leu Glu Glu Arg Ala
45                  50                  55                  60

GCC CGG AAC GTC TCT CAA GTT TCC AAG AAC TTG GAA AGC CAC CAC GGT        302
Ala Arg Asn Val Ser Gln Val Ser Lys Asn Leu Glu Ser His His Gly
                 65                  70                  75

GAC CAG ATG GCG CAG AAA TCC CAG TCC ACG CAG ATT TCA CAG GAA CTG        350
Asp Gln Met Ala Gln Lys Ser Gln Ser Thr Gln Ile Ser Gln Glu Leu
             80                  85                  90

GAG GAA CTT CGA GCT GAA CAG CAG AGA TTG AAA TCT CAG GAC TTG GAG        398
Glu Glu Leu Arg Ala Glu Gln Gln Arg Leu Lys Ser Gln Asp Leu Glu
         95                  100                 105

CTG TCC TGG AAC CTG AAC GGG CTT CAA GCA GAT CTG AGC AGC TTC AAG        446
Leu Ser Trp Asn Leu Asn Gly Leu Gln Ala Asp Leu Ser Ser Phe Lys
```

|  |  |  |  |  |  |  |  |  |  |  |  |  |  |  |
|---|---|---|---|---|---|---|---|---|---|---|---|---|---|---|
| 110 | | | | 115 | | | | | 120 | | | | | |
| TCC | CAG | GAA | TTG | AAC | GAG | AGG | AAC | GAA | GCT | TCA | GAT | TTG | CTG | GAA | AGA | 494
| Ser | Gln | Glu | Leu | Asn | Glu | Arg | Asn | Glu | Ala | Ser | Asp | Leu | Leu | Glu | Arg
| 125 | | | | 130 | | | | | 135 | | | | | 140 |
| CTC | CGC | GAG | GAG | GTG | ACA | AAG | CTA | AGG | ATG | GAG | TTG | CAG | GTC | TCC | AGC | 542
| Leu | Arg | Glu | Glu | Val | Thr | Lys | Leu | Arg | Met | Glu | Leu | Gln | Val | Ser | Ser
| | | | | 145 | | | | | 150 | | | | | 155 |
| GGC | TTT | GTG | TGC | AAC | ACG | TGC | CCT | GAA | AAG | TGG | ATC | AAT | TTC | CAA | CGC | 590
| Gly | Phe | Val | Cys | Asn | Thr | Cys | Pro | Glu | Lys | Trp | Ile | Asn | Phe | Gln | Arg
| | | | | 160 | | | | | 165 | | | | | 170 |
| AAG | TGC | TAC | TAC | TTC | GGC | AAG | GGC | ACC | AAG | CAG | TGG | GTC | CAC | GCC | CGG | 638
| Lys | Cys | Tyr | Tyr | Phe | Gly | Lys | Gly | Thr | Lys | Gln | Trp | Val | His | Ala | Arg
| | | 175 | | | | 180 | | | | | 185 | | | |
| TAT | GCC | TGT | GAC | GAC | ATG | GAA | GGG | CAG | CTG | GTC | AGC | ATC | CAC | AGC | CCG | 686
| Tyr | Ala | Cys | Asp | Asp | Met | Glu | Gly | Gln | Leu | Val | Ser | Ile | His | Ser | Pro
| | 190 | | | | 195 | | | | | 200 | | | | | |
| GAG | GAG | CAG | GAC | TTC | CTG | ACC | AAG | CAT | GCC | AGC | CAC | ACC | GGC | TCC | TGG | 734
| Glu | Glu | Gln | Asp | Phe | Leu | Thr | Lys | His | Ala | Ser | His | Thr | Gly | Ser | Trp
| 205 | | | | 210 | | | | | 215 | | | | | | 220 |
| ATT | GGC | CTT | CGG | AAC | TTG | GAC | CTG | AAG | GGA | GAG | TTT | ATC | TGG | GTG | GAT | 782
| Ile | Gly | Leu | Arg | Asn | Leu | Asp | Leu | Lys | Gly | Glu | Phe | Ile | Trp | Val | Asp
| | | | | 225 | | | | | 230 | | | | | 235 |
| GGG | AGC | CAT | GTG | GAC | TAC | AGC | AAC | TGG | GCT | CCA | GGG | GAG | CCC | ACC | AGC | 830
| Gly | Ser | His | Val | Asp | Tyr | Ser | Asn | Trp | Ala | Pro | Gly | Glu | Pro | Thr | Ser
| | | | 240 | | | | | 245 | | | | | 250 | | |
| CGG | AGC | CAG | GGC | GAG | GAC | TGC | GTG | ATG | ATG | CGG | GGC | TCC | GGT | CGC | TGG | 878
| Arg | Ser | Gln | Gly | Glu | Asp | Cys | Val | Met | Met | Arg | Gly | Ser | Gly | Arg | Trp
| | | 255 | | | | | 260 | | | | | 265 | | | |
| AAC | GAC | GCC | TTC | TGC | GAC | CGT | AAG | CTG | GGC | GCC | TGG | GTG | TGC | GAC | CGG | 926
| Asn | Asp | Ala | Phe | Cys | Asp | Arg | Lys | Leu | Gly | Ala | Trp | Val | Cys | Asp | Arg
| | 270 | | | | | 275 | | | | | 280 | | | | |
| CTG | GCC | ACA | TGC | ACG | CCG | CCA | GCC | AGC | GAA | GGT | TCC | GCG | GAG | TCC | ATG | 974
| Leu | Ala | Thr | Cys | Thr | Pro | Pro | Ala | Ser | Glu | Gly | Ser | Ala | Glu | Ser | Met
| 285 | | | | 290 | | | | | 295 | | | | | | 300 |
| GGA | CCT | GAT | TCA | AGA | CCA | GAC | CCT | GAC | GGC | CGC | CTG | CCC | ACC | CCC | TCT | 1022
| Gly | Pro | Asp | Ser | Arg | Pro | Asp | Pro | Asp | Gly | Arg | Leu | Pro | Thr | Pro | Ser
| | | | | 305 | | | | | 310 | | | | | 315 |
| GCC | CCT | CTC | CAC | TCT | | | | | | | | | | | | 1037
| Ala | Pro | Leu | His | Ser
| | | | | 320 |

( 2 ) INFORMATION FOR SEQ ID NO:8:

( i ) SEQUENCE CHARACTERISTICS:
        ( A ) LENGTH: 321 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| Met | Glu | Glu | Gly | Gln | Tyr | Ser | Glu | Ile | Glu | Glu | Leu | Pro | Arg | Arg | Arg |
|---|---|---|---|---|---|---|---|---|---|---|---|---|---|---|---|
| 1 | | | | 5 | | | | | 10 | | | | | 15 | |
| Cys | Cys | Arg | Arg | Gly | Thr | Gln | Ile | Val | Leu | Leu | Gly | Leu | Val | Thr | Ala |
| | | | 20 | | | | | 25 | | | | | 30 | | |
| Ala | Leu | Trp | Ala | Gly | Leu | Leu | Thr | Leu | Leu | Leu | Leu | Trp | His | Trp | Asp |
| | | 35 | | | | | 40 | | | | | 45 | | | |
| Thr | Thr | Gln | Ser | Leu | Lys | Gln | Leu | Glu | Glu | Arg | Ala | Ala | Arg | Asn | Val |
| | 50 | | | | | 55 | | | | | 60 | | | | |
| Ser | Gln | Val | Ser | Lys | Asn | Leu | Glu | Ser | His | His | Gly | Asp | Gln | Met | Ala |
| 65 | | | | | 70 | | | | | 75 | | | | | 80 |

-continued

```
Gln Lys Ser Gln Ser Thr Gln Ile Ser Gln Glu Leu Glu Glu Leu Arg
                85                  90                  95
Ala Glu Gln Gln Arg Leu Lys Ser Gln Asp Leu Glu Leu Ser Trp Asn
            100                 105                 110
Leu Asn Gly Leu Gln Ala Asp Leu Ser Ser Phe Lys Ser Gln Glu Leu
        115                 120                 125
Asn Glu Arg Asn Glu Ala Ser Asp Leu Leu Glu Arg Leu Arg Glu Glu
    130                 135                 140
Val Thr Lys Leu Arg Met Glu Leu Gln Val Ser Ser Gly Phe Val Cys
145                 150                 155                 160
Asn Thr Cys Pro Glu Lys Trp Ile Asn Phe Gln Arg Lys Cys Tyr Tyr
                165                 170                 175
Phe Gly Lys Gly Thr Lys Gln Trp Val His Ala Arg Tyr Ala Cys Asp
            180                 185                 190
Asp Met Glu Gly Gln Leu Val Ser Ile His Ser Pro Glu Glu Gln Asp
        195                 200                 205
Phe Leu Thr Lys His Ala Ser His Thr Gly Ser Trp Ile Gly Leu Arg
    210                 215                 220
Asn Leu Asp Leu Lys Gly Glu Phe Ile Trp Val Asp Gly Ser His Val
225                 230                 235                 240
Asp Tyr Ser Asn Trp Ala Pro Gly Glu Pro Thr Ser Arg Ser Gln Gly
                245                 250                 255
Glu Asp Cys Val Met Met Arg Gly Ser Gly Arg Trp Asn Asp Ala Phe
            260                 265                 270
Cys Asp Arg Lys Leu Gly Ala Trp Val Cys Asp Arg Leu Ala Thr Cys
        275                 280                 285
Thr Pro Pro Ala Ser Glu Gly Ser Ala Glu Ser Met Gly Pro Asp Ser
    290                 295                 300
Arg Pro Asp Pro Asp Gly Arg Leu Pro Thr Pro Ser Ala Pro Leu His
305                 310                 315                 320
Ser
```

( 2 ) INFORMATION FOR SEQ ID NO:9:

( i ) SEQUENCE CHARACTERISTICS:
        ( A ) LENGTH: 1025 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 66..1025

( x i ) SEQUENCE DESCRIPTION: SEQ ID NO:9:

```
GCGGGGACGC AATAGAGTCA GAGGCCAAAT AGAACAGGAA CTTGGAACAA GCAGAATTTA         60

GCATA ATG AAT CCT CCA AGC CAG GAG ATC GAG GAG CTT CCC AGG AGG          107
      Met Asn Pro Pro Ser Gln Glu Ile Glu Glu Leu Pro Arg Arg
       1               5                  10

CGG TGT TGC AGG CGT GGG ACT CAG ATC GTG CTG CTG GGG CTG GTG ACC        155
Arg Cys Cys Arg Arg Gly Thr Gln Ile Val Leu Leu Gly Leu Val Thr
 15                  20                  25                  30

GCC GCT CTG TGG GCT GGC CTG CTG ACT CTG CTT CTC CTG TGG CAC TGG        203
```

| | | | | | | | | | | | | | | | | |
|---|---|---|---|---|---|---|---|---|---|---|---|---|---|---|---|---|
| Ala | Ala | Leu | Trp | Ala<br>35 | Gly | Leu | Leu | Thr | Leu<br>40 | Leu | Leu | Leu | Trp | His<br>45 | Trp | |
| GAC | ACC | ACA | CAG | AGT | CTA | AAA | CAG | CTG | GAA | GAG | AGG | GCT | GCC | CGG | AAC | 251 |
| Asp | Thr | Thr | Gln<br>50 | Ser | Leu | Lys | Gln | Leu<br>55 | Glu | Glu | Arg | Ala | Ala<br>60 | Arg | Asn | |
| GTC | TCT | CAA | GTT | TCC | AAG | AAC | TTG | GAA | AGC | CAC | CAC | GGT | GAC | CAG | ATG | 299 |
| Val | Ser | Gln<br>65 | Val | Ser | Lys | Asn | Leu<br>70 | Glu | Ser | His | His | Gly<br>75 | Asp | Gln | Met | |
| GCG | CAG | AAA | TCC | CAG | TCC | ACG | CAG | ATT | TCA | CAG | GAA | CTG | GAG | GAA | CTT | 347 |
| Ala | Gln<br>80 | Lys | Ser | Gln | Ser<br>85 | Thr | Gln | Ile | Ser | Gln<br>90 | Glu | Leu | Glu | Glu | Leu | |
| CGA | GCT | GAA | CAG | CAG | AGA | TTG | AAA | TCT | CAG | GAC | TTG | GAG | CTG | TCC | TGG | 395 |
| Arg<br>95 | Ala | Glu | Gln | Gln | Arg<br>100 | Leu | Lys | Ser | Gln | Asp<br>105 | Leu | Glu | Leu | Ser | Trp<br>110 | |
| AAC | CTG | AAC | GGG | CTT | CAA | GCA | GAT | CTG | AGC | AGC | TTC | AAG | TCC | CAG | GAA | 443 |
| Asn | Leu | Asn | Gly | Leu<br>115 | Gln | Ala | Asp | Leu | Ser<br>120 | Ser | Phe | Lys | Ser | Gln<br>125 | Glu | |
| TTG | AAC | GAG | AGG | AAC | GAA | GCT | TCA | GAT | TTG | CTG | GAA | AGA | CTC | CGC | GAG | 491 |
| Leu | Asn | Glu | Arg<br>130 | Asn | Glu | Ala | Ser | Asp<br>135 | Leu | Leu | Glu | Arg | Leu<br>140 | Arg | Glu | |
| GAG | GTG | ACA | AAG | CTA | AGG | ATG | GAG | TTG | CAG | GTC | TCC | AGC | GGC | TTT | GTG | 539 |
| Glu | Val | Thr<br>145 | Lys | Leu | Arg | Met | Glu<br>150 | Leu | Gln | Val | Ser | Ser<br>155 | Gly | Phe | Val | |
| TGC | AAC | ACG | TGC | CCT | GAA | AAG | TGG | ATC | AAT | TTC | CAA | CGC | AAG | TGC | TAC | 587 |
| Cys | Asn<br>160 | Thr | Cys | Pro | Glu | Lys<br>165 | Trp | Ile | Asn | Phe | Gln<br>170 | Arg | Lys | Cys | Tyr | |
| TAC | TTC | GGC | AAG | GGC | ACC | AAG | CAG | TGG | GTC | CAC | GCC | CGG | TAT | GCC | TGT | 635 |
| Tyr<br>175 | Phe | Gly | Lys | Gly | Thr<br>180 | Lys | Gln | Trp | Val | His<br>185 | Ala | Arg | Tyr | Ala | Cys<br>190 | |
| GAC | GAC | ATG | GAA | GGG | CAG | CTG | GTC | AGC | ATC | CAC | AGC | CCG | GAG | GAG | CAG | 683 |
| Asp | Asp | Met | Glu | Gly<br>195 | Gln | Leu | Val | Ser | Ile<br>200 | His | Ser | Pro | Glu | Glu<br>205 | Gln | |
| GAC | TTC | CTG | ACC | AAG | CAT | GCC | AGC | CAC | ACC | GGC | TCC | TGG | ATT | GGC | CTT | 731 |
| Asp | Phe | Leu | Thr<br>210 | Lys | His | Ala | Ser | His<br>215 | Thr | Gly | Ser | Trp | Ile<br>220 | Gly | Leu | |
| CGG | AAC | TTG | GAC | CTG | AAG | GGA | GAG | TTT | ATC | TGG | GTG | GAT | GGG | AGC | CAT | 779 |
| Arg | Asn | Leu<br>225 | Asp | Leu | Lys | Gly | Glu<br>230 | Phe | Ile | Trp | Val | Asp<br>235 | Gly | Ser | His | |
| GTG | GAC | TAC | AGC | AAC | TGG | GCT | CCA | GGG | GAG | CCC | ACC | AGC | CGG | AGC | CAG | 827 |
| Val | Asp<br>240 | Tyr | Ser | Asn | Trp | Ala<br>245 | Pro | Gly | Glu | Pro | Thr<br>250 | Ser | Arg | Ser | Gln | |
| GGC | GAG | GAC | TGC | GTG | ATG | ATG | CGG | GGC | TCC | GGT | CGC | TGG | AAC | GAC | GCC | 875 |
| Gly<br>255 | Glu | Asp | Cys | Val | Met<br>260 | Met | Arg | Gly | Ser | Gly<br>265 | Arg | Trp | Asn | Asp | Ala<br>270 | |
| TTC | TGC | GAC | CGT | AAG | CTG | GGC | GCC | TGG | GTG | TGC | GAC | CGG | CTG | GCC | ACA | 923 |
| Phe | Cys | Asp | Arg | Lys<br>275 | Leu | Gly | Ala | Trp | Val<br>280 | Cys | Asp | Arg | Leu | Ala<br>285 | Thr | |
| TGC | ACG | CCG | CCA | GCC | AGC | GAA | GGT | TCC | GCG | GAG | TCC | ATG | GGA | CCT | GAT | 971 |
| Cys | Thr | Pro | Pro<br>290 | Ala | Ser | Glu | Gly | Ser<br>295 | Ala | Glu | Ser | Met | Gly<br>300 | Pro | Asp | |
| TCA | AGA | CCA | GAC | CCT | GAC | GGC | CGC | CTG | CCC | ACC | CCC | TCT | GCC | CCT | CTC | 1019 |
| Ser | Arg | Pro<br>305 | Asp | Pro | Asp | Gly | Arg<br>310 | Leu | Pro | Thr | Pro | Ser<br>315 | Ala | Pro | Leu | |
| CAC | TCT | | | | | | | | | | | | | | | 1025 |
| His | Ser<br>320 | | | | | | | | | | | | | | | |

( 2 ) INFORMATION FOR SEQ ID NO:10:

( i ) SEQUENCE CHARACTERISTICS:

( A ) LENGTH: 320 amino acids ( B ) TYPE: amino acid
( D ) TOPOLOGY: linear ( i i ) MOLECULE TYPE: protein ( x i ) SEQUENCE DESCRIPTION: SEQ ID NO:10:

| Met 1 | Asn | Pro | Pro | Ser 5 | Gln | Glu | Ile | Glu | Leu 10 | Pro | Arg | Arg | Arg | Cys 15 |
| Cys | Arg | Arg | Gly 20 | Thr | Gln | Ile | Val | Leu 25 | Leu | Gly | Leu | Val | Thr 30 | Ala | Ala |
| Leu | Trp | Ala 35 | Gly | Leu | Leu | Thr | Leu 40 | Leu | Leu | Leu | Trp | His 45 | Trp | Asp | Thr |
| Thr | Gln 50 | Ser | Leu | Lys | Gln | Leu 55 | Glu | Glu | Arg | Ala | Ala 60 | Arg | Asn | Val | Ser |
| Gln 65 | Val | Ser | Lys | Asn | Leu 70 | Glu | Ser | His | His | Gly 75 | Asp | Gln | Met | Ala | Gln 80 |
| Lys | Ser | Gln | Ser | Thr 85 | Gln | Ile | Ser | Gln | Glu 90 | Leu | Glu | Glu | Leu | Arg 95 | Ala |
| Glu | Gln | Gln | Arg 100 | Leu | Lys | Ser | Gln | Asp 105 | Leu | Glu | Leu | Ser | Trp 110 | Asn | Leu |
| Asn | Gly | Leu 115 | Gln | Ala | Asp | Leu | Ser 120 | Ser | Phe | Lys | Ser | Gln 125 | Glu | Leu | Asn |
| Glu | Arg 130 | Asn | Glu | Ala | Ser | Asp 135 | Leu | Leu | Glu | Arg | Leu 140 | Arg | Glu | Glu | Val |
| Thr 145 | Lys | Leu | Arg | Met | Glu 150 | Leu | Gln | Val | Ser | Ser 155 | Gly | Phe | Val | Cys | Asn 160 |
| Thr | Cys | Pro | Glu | Lys 165 | Trp | Ile | Asn | Phe | Gln 170 | Arg | Lys | Cys | Tyr | Tyr 175 | Phe |
| Gly | Lys | Gly | Thr 180 | Lys | Gln | Trp | Val | His 185 | Ala | Arg | Tyr | Ala | Cys 190 | Asp | Asp |
| Met | Glu | Gly 195 | Gln | Leu | Val | Ser | Ile 200 | His | Ser | Pro | Glu | Glu 205 | Gln | Asp | Phe |
| Leu | Thr 210 | Lys | His | Ala | Ser | His 215 | Thr | Gly | Ser | Trp | Ile 220 | Gly | Leu | Arg | Asn |
| Leu 225 | Asp | Leu | Lys | Gly | Glu 230 | Phe | Ile | Trp | Val | Asp 235 | Gly | Ser | His | Val | Asp 240 |
| Tyr | Ser | Asn | Trp | Ala 245 | Pro | Gly | Glu | Pro | Thr 250 | Ser | Arg | Ser | Gln | Gly 255 | Glu |
| Asp | Cys | Val | Met 260 | Met | Arg | Gly | Ser | Gly 265 | Arg | Trp | Asn | Asp | Ala 270 | Phe | Cys |
| Asp | Arg | Lys 275 | Leu | Gly | Ala | Trp | Val 280 | Cys | Asp | Arg | Leu | Ala 285 | Thr | Cys | Thr |
| Pro | Pro 290 | Ala | Ser | Glu | Gly | Ser 295 | Ala | Glu | Ser | Met | Gly 300 | Pro | Asp | Ser | Arg |
| Pro 305 | Asp | Pro | Asp | Gly | Arg 310 | Leu | Pro | Thr | Pro | Ser 315 | Ala | Pro | Leu | His | Ser 320 |

( 2 ) INFORMATION FOR SEQ ID NO:11:

( i ) SEQUENCE CHARACTERISTICS:
( A ) LENGTH: 501 base pairs
( B ) TYPE: nucleic acid
( C ) STRANDEDNESS: single
( D ) TOPOLOGY: linear ( i i ) MOLECULE TYPE: cDNA ( i i i ) HYPOTHETICAL: NO (iv) ANTI-SENSE: NO (ix) FEATURE:
    (A) NAME/KEY: CDS
    (B) LOCATION: 1..501

(xi) SEQUENCE DESCRIPTION: SEQ ID NO:11:

| ATG | GAG | GAA | GGT | CAA | TAT | TCA | GAC | TGG | GAC | ACC | ACA | CAG | AGT | CTA | AAA | 48 |
| Met | Glu | Glu | Gly | Gln | Tyr | Ser | Asp | Trp | Asp | Thr | Thr | Gln | Ser | Leu | Lys | |
| 1 | | | | 5 | | | | | 10 | | | | | 15 | | |

| CAG | CTG | GAA | GAG | AGG | GCT | GCC | CGG | AAC | GTC | TCT | CAA | GTT | TCC | AAG | AAC | 96 |
| Gln | Leu | Glu | Glu | Arg | Ala | Ala | Arg | Asn | Val | Ser | Gln | Val | Ser | Lys | Asn | |
| | | | 20 | | | | | 25 | | | | | 30 | | | |

| TTG | GAA | AGC | CAC | CAC | GGT | GAC | CAG | ATG | GCG | CAG | AAA | TCC | CAG | TCC | ACG | 144 |
| Leu | Glu | Ser | His | His | Gly | Asp | Gln | Met | Ala | Gln | Lys | Ser | Gln | Ser | Thr | |
| | | 35 | | | | | 40 | | | | | 45 | | | | |

| CAG | ATT | TCA | CAG | GAA | CTG | GAG | GAA | CTT | CGA | GCT | GAA | CAG | CAG | AGA | TTG | 192 |
| Gln | Ile | Ser | Gln | Glu | Leu | Glu | Glu | Leu | Arg | Ala | Glu | Gln | Gln | Arg | Leu | |
| | 50 | | | | | 55 | | | | | 60 | | | | | |

| AAA | TCT | CAG | GAC | TTG | GAG | CTG | TCC | TGG | AAC | CTG | AAC | GGG | CTT | CAA | GCA | 240 |
| Lys | Ser | Gln | Asp | Leu | Glu | Leu | Ser | Trp | Asn | Leu | Asn | Gly | Leu | Gln | Ala | |
| 65 | | | | | 70 | | | | | 75 | | | | | 80 | |

| GAT | CTG | AGC | AGC | TTC | AAG | TCC | CAG | GAA | TTG | AAC | GAG | AGG | AAC | GAA | GCT | 288 |
| Asp | Leu | Ser | Ser | Phe | Lys | Ser | Gln | Glu | Leu | Asn | Glu | Arg | Asn | Glu | Ala | |
| | | | | 85 | | | | | 90 | | | | | 95 | | |

| TCA | GAT | TTG | CTG | GAA | AGA | CTC | CGC | GAG | GAG | GTG | ACA | AAG | CTA | AGG | ATG | 336 |
| Ser | Asp | Leu | Leu | Glu | Arg | Leu | Arg | Glu | Glu | Val | Thr | Lys | Leu | Arg | Met | |
| | | | 100 | | | | | 105 | | | | | 110 | | | |

| GAG | TTG | CAG | GTC | TCC | AGC | GGC | TTT | GTG | TGC | AAC | ACG | TGC | CCT | GAA | AAG | 384 |
| Glu | Leu | Gln | Val | Ser | Ser | Gly | Phe | Val | Cys | Asn | Thr | Cys | Pro | Glu | Lys | |
| | | 115 | | | | | 120 | | | | | 125 | | | | |

| TGG | ATC | AAT | TTC | BAA | CGC | AAG | TGC | TAC | TAC | TTC | GGC | AAG | GGC | ACC | AAG | 432 |
| Trp | Ile | Asn | Phe | Gln | Arg | Lys | Cys | Tyr | Tyr | Phe | Gly | Lys | Gly | Thr | Lys | |
| | 130 | | | | | 135 | | | | | 140 | | | | | |

| CAG | TGG | GTC | CAC | GCC | CGG | TAT | GCC | TGT | GAC | GAC | ATG | GAA | GGG | CAG | CTG | 480 |
| Gln | Trp | Val | His | Ala | Arg | Tyr | Ala | Cys | Asp | Asp | Met | Glu | Gly | Gln | Leu | |
| 145 | | | | | 150 | | | | | 155 | | | | | 160 | |

| GTC | AGC | ATC | CAC | AGC | CCG | GAG | | | | | | | | | | 501 |
| Val | Ser | Ile | His | Ser | Pro | Glu | | | | | | | | | | |
| | | | | 165 | | | | | | | | | | | | |

(2) INFORMATION FOR SEQ ID NO:12:

(i) SEQUENCE CHARACTERISTICS:
        (A) LENGTH: 167 amino acids
        (B) TYPE: amino acid
        (D) TOPOLOGY: linear (ii) MOLECULE TYPE: protein (xi) SEQUENCE DESCRIPTION: SEQ ID NO:12:

| Met | Glu | Glu | Gly | Gln | Tyr | Ser | Asp | Trp | Asp | Thr | Thr | Gln | Ser | Leu | Lys |
| 1 | | | | 5 | | | | | 10 | | | | | 15 | |

| Gln | Leu | Glu | Glu | Arg | Ala | Ala | Arg | Asn | Val | Ser | Gln | Val | Ser | Lys | Asn |
| | | | 20 | | | | | 25 | | | | | 30 | | |

| Leu | Glu | Ser | His | His | Gly | Asp | Gln | Met | Ala | Gln | Lys | Ser | Gln | Ser | Thr |
| | | 35 | | | | | 40 | | | | | 45 | | | |

| Gln | Ile | Ser | Gln | Glu | Leu | Glu | Glu | Leu | Arg | Ala | Glu | Gln | Gln | Arg | Leu |
| | 50 | | | | | 55 | | | | | 60 | | | | |

| Lys | Ser | Gln | Asp | Leu | Glu | Leu | Ser | Trp | Asn | Leu | Asn | Gly | Leu | Gln | Ala |
| 65 | | | | | 70 | | | | | 75 | | | | | 80 |

| Asp | Leu | Ser | Ser | Phe | Lys | Ser | Gln | Glu | Leu | Asn | Glu | Arg | Asn | Glu | Ala |

|  | | | | | 85 | | | | 90 | | | | | 95 | |
|---|---|---|---|---|---|---|---|---|---|---|---|---|---|---|---|
| Ser | Asp | Leu | Leu<br>100 | Glu | Arg | Leu | Arg | Glu<br>105 | Glu | Val | Thr | Lys | Leu<br>110 | Arg | Met |
| Glu | Leu | Gln<br>115 | Val | Ser | Ser | Gly | Phe<br>120 | Val | Cys | Asn | Thr | Cys<br>125 | Pro | Glu | Lys |
| Trp | Ile<br>130 | Asn | Phe | Gln | Arg | Lys<br>135 | Cys | Tyr | Tyr | Phe | Gly<br>140 | Lys | Gly | Thr | Lys |
| Gln<br>145 | Trp | Val | His | Ala | Arg<br>150 | Tyr | Ala | Cys | Asp | Asp<br>155 | Met | Glu | Gly | Gln | Leu<br>160 |
| Val | Ser | Ile | His | Ser<br>165 | Pro | Glu | | | | | | | | | |

( 2 ) INFORMATION FOR SEQ ID NO:13:

( i ) SEQUENCE CHARACTERISTICS:
        ( A ) LENGTH: 498 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 1..498

( x i ) SEQUENCE DESCRIPTION: SEQ ID NO:13:

| ATG | AAT | CCT | CCA | AGC | CAG | GAC | TGG | GAC | ACC | ACA | CAG | AGT | CTA | AAA | CAG | 48 |
|---|---|---|---|---|---|---|---|---|---|---|---|---|---|---|---|---|
| Met<br>1 | Asn | Pro | Pro | Ser<br>5 | Gln | Asp | Trp | Asp | Thr<br>10 | Thr | Gln | Ser | Leu | Lys<br>15 | Gln | |
| CTG | GAA | GAG | AGG | GCT | GCC | CGG | AAC | GTC | TCT | CAA | GTT | TCC | AAG | AAC | TTG | 96 |
| Leu | Glu | Glu | Arg<br>20 | Ala | Ala | Arg | Asn | Val<br>25 | Ser | Gln | Val | Ser | Lys<br>30 | Asn | Leu | |
| GAA | AGC | CAC | CAC | GGT | GAC | CAG | ATG | GCG | CAG | AAA | TCC | CAG | TCC | ACG | CAG | 144 |
| Glu | Ser | His<br>35 | His | Gly | Asp | Gln | Met<br>40 | Ala | Gln | Lys | Ser | Gln<br>45 | Ser | Thr | Gln | |
| ATT | TCA | CAG | GAA | CTG | GAG | GAA | CTT | CGA | GCT | GAA | CAG | CAG | AGA | TTG | AAA | 192 |
| Ile | Ser<br>50 | Gln | Glu | Leu | Glu | Glu<br>55 | Leu | Arg | Ala | Glu | Gln<br>60 | Gln | Arg | Leu | Lys | |
| TCT | CAG | GAC | TTG | GAG | CTG | TCC | TGG | AAC | CTG | AAC | GGG | CTT | CAA | GCA | GAT | 240 |
| Ser<br>65 | Gln | Asp | Leu | Glu | Leu<br>70 | Ser | Trp | Asn | Leu | Asn<br>75 | Gly | Leu | Gln | Ala | Asp<br>80 | |
| CTG | AGC | AGC | TTC | AAG | TCC | CAG | GAA | TTG | AAC | GAG | AGG | AAC | GAA | GCT | TCA | 288 |
| Leu | Ser | Ser | Phe | Lys<br>85 | Ser | Gln | Glu | Leu | Asn<br>90 | Glu | Arg | Asn | Glu | Ala<br>95 | Ser | |
| GAT | TTG | CTG | GAA | AGA | CTC | CGC | GAG | GAG | GTG | ACA | AAG | CTA | AGG | ATG | GAG | 336 |
| Asp | Leu | Leu | Glu<br>100 | Arg | Leu | Arg | Glu | Glu<br>105 | Val | Thr | Lys | Leu | Arg<br>110 | Met | Glu | |
| TTG | CAG | GTC | TCC | AGC | GGC | TTT | GTG | TGC | AAC | ACG | TGC | CCT | GAA | AAG | TGG | 384 |
| Leu | Gln | Val<br>115 | Ser | Ser | Gly | Phe | Val<br>120 | Cys | Asn | Thr | Cys | Pro<br>125 | Glu | Lys | Trp | |
| ATC | AAT | TTC | CAA | CGC | AAG | TGC | TAC | TAC | TTC | GGC | AAG | GGC | ACC | AAG | CAG | 432 |
| Ile | Asn<br>130 | Phe | Gln | Arg | Lys | Cys<br>135 | Tyr | Tyr | Phe | Gly | Lys<br>140 | Gly | Thr | Lys | Gln | |
| TGG | GTC | CAC | GCC | CGG | TAT | GCC | TGT | GAC | GAC | ATG | GAA | GGG | CAG | CTG | GTC | 480 |
| Trp<br>145 | Val | His | Ala | Arg<br>150 | Tyr | Ala | Cys | Asp | Asp<br>155 | Met | Glu | Gly | Gln | Leu<br>160 | Val | |
| AGC | ATC | CAC | AGC | CCG | GAG | | | | | | | | | | | 498 |
| Ser | Ile | His | Ser | Pro | Glu | | | | | | | | | | | |

( 2 ) INFORMATION FOR SEQ ID NO:14:

( i ) SEQUENCE CHARACTERISTICS:
        ( A ) LENGTH: 166 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Met Asn Pro Pro Ser Gln Asp Trp Asp Thr Thr Gln Ser Leu Lys Gln
 1               5                  10                  15

Leu Glu Glu Arg Ala Ala Arg Asn Val Ser Gln Val Ser Lys Asn Leu
            20                  25                  30

Glu Ser His His Gly Asp Gln Met Ala Gln Lys Ser Gln Ser Thr Gln
        35                  40                  45

Ile Ser Gln Glu Leu Glu Glu Leu Arg Ala Glu Gln Gln Arg Leu Lys
    50                  55                  60

Ser Gln Asp Leu Glu Leu Ser Trp Asn Leu Asn Gly Leu Gln Ala Asp
65                  70                  75                  80

Leu Ser Ser Phe Lys Ser Gln Glu Leu Asn Glu Arg Asn Glu Ala Ser
                85                  90                  95

Asp Leu Leu Glu Arg Leu Arg Glu Glu Val Thr Lys Leu Arg Met Glu
            100                 105                 110

Leu Gln Val Ser Ser Gly Phe Val Cys Asn Thr Cys Pro Glu Lys Trp
        115                 120                 125

Ile Asn Phe Gln Arg Lys Cys Tyr Tyr Phe Gly Lys Gly Thr Lys Gln
    130                 135                 140

Trp Val His Ala Arg Tyr Ala Cys Asp Asp Met Glu Gly Gln Leu Val
144                 150                 155                 160

Ser Ile His Ser Pro Glu
            165
```

DNA SEQUENCES FOR SOLUBLE FORM OF CD23

CROSS-REFERENCE TO A RELATED APPLICATION

This application is a continuation-in-part application of U.S. patent application Ser. No. 07/931,142 filed Aug. 17, 1992, now abandoned.

GRANT REFERENCE

Work on the invention described herein was funded in part by the National Institute of Health, contract number CA 49229-03. The United States Government may have certain rights in the invention.

BACKGROUND OF THE INVENTION

The present invention relates generally to the manipulation of genetic materials and, more particularly, to the discovery, isolation, and purification of a DNA sequence which codes upon expression a soluble form of the regulatory protein CD23, making possible the production of proteins possessing one or more of the biological properties of naturally-occurring soluble CD23.

BACKGROUND OF MOLECULAR BIOLOGY

Genetic materials are broadly defined as the chemicals which program for and guide the manufacture of the constituents and direct the responses of cells. A long chain composed of nucleotides called deoxyribonucleic (DNA) comprises this genetic material. DNA consists of repeating units of four different nucleotides, adenine, guanine, thymine or cytosine which are bound to a deoxyribose sugar to which a phosphate group is attached. Functional DNA occurs in the form of a stable double-stranded association of single-strands of nucleotides. The associations occur by means of hydrogen bonding between "complimentary" nucleotide basis existing between adenine (A) and thymine (T) or guanine, (G) and cytosine (C). The manufacture of cell components and proteins is effected through a process where the DNA nucleotide sequences are "transcribed" into relatively unstable messenger RNA (mRNA) by hydrogen pairing of complimentary bases of adenine, uracil, guanine and cytosine to an unhybridized coding strand of DNA. The double-stranded DNA disassociates into single strands and only one strand of the DNA is transcribed into messenger RNA.

The mRNA in turn serves as a template for the formation of proteins in the ribosomes. This is the process of mRNA translation. All DNA sequences do not all necessarily code for proteins. There are several noncoding regions of DNA which control transcription such as promoter regions, regulator regions, and control sequences, which are not transcribed into the mRNA.

These sequences are called introns and are disbursed between the coding segments of the DNA. Those segments which do encode proteins are termed exons. It is these exons that are transcribed into the messenger for the RNA for translation into proteins. Thus the mRNA more directly codes the protein due to the omission of intron sequences. By alternative exon usage, different forms of proteins may be translated. Therefore an analysis of the mRNA transcripts transcribed from DNA will identify what proteins are being translated or expressed by the cell, including any isoforms due to alternative exon usage.

THE PROTEIN CD23

The glycoprotein CD23 has generated much interest among molecular immunologists due to its immuno-regulatory functions. Evidence of this interest is reflected by the fact that almost simultaneously three laboratories published the nucleotide sequence of the cloned cDNA. (Kikutani et al., 1986, Molecular Structure of Human Lymphocyte Receptor for Immunoglobulin, *E. Cell* 47: 657–65); (Ikuta, K. et al., 1987, Human Lymphocyte Fc Receptor for IgE; Sequence Homology of its Cloned cDNA With Animal Lectins. *Proc. Natl. Acad. Sci. USA* 84: 819–23) both of which are incorporated herein by reference.

CD23 or FcεII has been demonstrated to be an integral membrane protein on human and rodent B lymphocytes, the precursors of plasma cells, which create antibodies (or immunoglobulins) responsible for the humoral immune response. (Fritsche, R., and Spiegelberg, 1978, Fc Receptors for IgE on Normal Rat Lymphocytes, *J. Immunol.* 121.471–478); (Yodoi, J., Ishizaka, K. 1980, Induction of Fce-Receptor Bearing Cells in vitro in Human Peripheral Lymphocytes, *J. Immunol.* 124: 934–938); Kotona, et al. 1984, Characterization of Murine Lymphocyte IgE Receptors by Flor Microfluorometry. *J. Immunol.* 133: 1521–28); Bonnefoy et al, 1987, Production and Characterization of a Monoclonal Antibody Specific for the Human Lymphocyte Low Affinity Receptor for IgE: CD23 is a Low Affinity Receptor for IgE. *J. Immunol,* 138: 2970–2978); Yukawa et al, 1987, A B Cell-Specific Differentiation Antigen, CD23 is a Receptor for IgE(FceR) on Lymphocytes, *J. Immunol,* 138: 2576–1580). Additionally, CD23 has been found to be present on membranes of T-cells, or T lymphocytes, which regulate β-lymphocytes. In humans, CD23 has been found to be expressed in several types of hemopoietic cells, including platelets, dendritic cells, thymic epithelium, eosinophils, and monocytes (Caprin et al. 1977, Interaction Between IgE Complexes and Macrophages in the Rat: a New Mechanism of Macrophage Activation. *Eur. J. Immunol.* 7: 315–30); (Vercelli, D. et al, 1988, Human Recombinant Interleukin-4 Induces Fc-R2/CD23 in Normal Human Monocytes, *J. Exp. Med.* 167: 1406–16); (Beiber, et al, 1989, Induction of FcR2/CD23 on Human Epidermal Langerhan's Cells by Recombinant Interleukin 4 and α-Interferon, *J. Exp. Med.* 170: 309–14); (Hosoda, et al, 1989, Differential Regulation of the low affinity Fc Receptor for IgE (FcR2/CD23) and the H-2 Receptor (Tac/p55) on Eosinophilic Leukemia Cell Line (Eol-1 and Eol-3), *J. Immunol.* 143: 147–52). CD23 acts as a low affinity receptor on the surface of these cells which binds a type of specific immunoglobulin, immunoglobulin E (IgE).

Immunoglobulin E is responsible for the pathology of allergy. While this antibody is essential in conferring protection against parasites, the presence of excess IgE seems to result in the characteristic allergic response. People with allergies traditionally have abnormalities in CD23. Thus, it appears that CD23 is an important regulatory tool in controlling the amount of IgE present in the blood stream.

The amino acids of CD23 in both mice and humans are divided into three regions or domains: cytoplasmic, transmembrane and extra-cellular. The cytoplasmic segment containing the amino terminus consists of a series of amino acids encoded by a protein coding segment of the gene termed exon 2. Some remaining amino acids of the cytoplasmic domain and all amino acids of the transmembrane segment are encoded by exon 3. The transmembrane segment contains a series of hydrophilic residues after a heavily charged region which firmly anchors the protein in the bi-lipid membrane. The amino acids of the extra-cellular domain are encoded by exons 4–12 (Gollnick, et al. Isolation, Characterization and Expression of cDNA Clones Encoding the Mouse Fc Receptor for IgE (FcεII). *J. Immu-* nol. 144: 1974) SEQ ID NO:1 (position 151–1156) Ikuta, et al, Human Lymphocyte Fc Receptor for IgE sequence Homology of its Cloned cDNA. *Proc. Natl. Acad. Sci USA* 84, 819 1987. (see FIG. No. 1). The extra-cellular domain contains the IgE binding region.

Recently it was discovered that a smaller form of CD23, soluble CD23, was present in the supernatant of B lymphocytes. This smaller soluble form contained the IgE binding extra-cellular segment of the traditional membrane bound CD23 and still binds IgE. It was later concluded that proteolytic cleavage of the membrane bound CD23 gave rise to the soluble IgE binding factors, soluble CD23. (Fridman, et al, 1980, Interferon Enhances the Expression of Fc Receptors, *J. Immunol.* 124: 2436–2441).

This invention is based on the discovery that contrary to earlier thought, the smaller soluble form of CD23 present in the supernatant of centrifuged beta cells is not enzymatically cleaved from traditional membrane bound CD23, but is in fact, a protein translated from a transcript generated by alternative exon usage and mRNA splicing of the traditional CD23 gene. mRNA for different isoforms of CD23 were discovered and isolated from several hemeopoietic cells of mice and humans.

These mRNA transcripts omitted exon 3 of the CD23 gene, the exon which coded for the anchor and hydrophilic segments allowing tight association with the membrane. The resulting translated soluble CD23 contained the extra-cellular binding region and the intra-cellular region which interacts with the machinery of the cell, contrary to a segment generated by cleavage which would only contain the extra-cellular region.

The presence of mRNA for soluble CD23 is of great significance in that it demonstrates that the cell itself is actually manufacturing the smaller soluble CD23, and that the mRNA can be cloned as cDNA by use of reverse transcriptase, a polymerase chain reaction, (PCR) resulting in a nucleotide sequence of cDNA and thus the key to large scale synthesis of the molecules, CD23 which is without the hydrophilic segments which is encoded by exon 3.

It is an objective of the present invention to make possible the manufacture of large scale synthesis of the soluble form of CD23 which maintains its IgE binding capacity as it retains the region known to be responsible for IgE binding. Such a protein has a wide variety of uses, including a model for study of the properties of CD23, its IgE binding characteristics, use to study differentiation of B lymphocytes and ultimately the CD23 can also be used to identify compounds which would have the same binding characteristics as IgE for use as a pharmacologic and therapeutic agent in allergic diseases and other immunological disorders, due to the properties of soluble CD23 to bind and regulate IgE.

Another objective of the invention is to provide an extra-cellular means of regulating IgE production in humans.

Another objective of the invention is to isolate and purify the DNA sequences for soluble forms of CD23, which through cloning can make possible the generation of large amounts of soluble CD23.

Yet another object of the invention is to provide a vector containing the soluble CD23 gene sequence which may be cloned into virus or bacteria for amplification or the gene product.

The method and manner of accomplishing these and other objectives will become apparent from the detailed description of the invention which follows.

BRIEF SUMMARY OF THE INVENTION

The present invention provides for the first time novel purified and isolated nucleotide sequences which code upon translation soluble forms of the protein CD23. The sequences are disclosed. The invention also contemplates sequences which hybridize under stringent conditions to the disclosed sequences. Stringent hybridization conditions are known to those of skill in the art. The invention provides the means to produce protein products without the amino acids encoded by exon 3, the product retains the IgE binding function of traditional membrane bound CD23 in addition to the intra-cellular cell interaction machinery portion of CD23. Synthesis of these products will allow for production of CD23 forms which have one or more of the biologic properties of naturally occurring soluble CD23 including allelic variants thereof.

According to the present invention, DNA sequences which code upon expression part or all of the amino acid sequence of human and mouse soluble isoform of CD23 have been isolated and characterized. These isolated DNA sequences may then be transformed into compatible unicellular host organisms resulting in the expression of exogenous DNA providing large scale synthesis of this protein. The protein may then be harvested and used in pharmaceutical compositions for treatment of IgE mediated diseases, such as asthma, and other allergic responses or as a model for further study of CD23 binding mechanisms and its functional characteristics.

Analysis and cloning of mRNA molecules as cDNA produced gene sequences which had omitted exon 3, which codes for the transmembrane hydrophilic region, and the highly charged membrane anchor region, leading to production of a truncated soluble isoform of the CD23 protein.

BRIEF DESCRIPTION OF THE DRAWINGS

FIG. 1 is a schematic representation of mouse CD23 isoforms: Isoform A-SEQ ID NO:2, residues 1–55; Isoform B-SEQ ID NO:4, residues 1–15; Isoform C-SEQ ID NO:6, residues 1–28.

FIG. 2 is a schematic illustrating the primers used for isolation of mouse cDNA sequences and expected PCR products.

FIG. 3(a) and (b) is the cDNA sequence for Isoform A of mouse CD23 SEQ ID NO:1. For all sequences, Exon 3 is shown in bold. Splice junction sites are shown with arrows and underlined bases illustrate changes in sequence due to alternative Exon usage.

FIG. 4(a) and (b) is the cDNA sequence for Isoform B of mouse CD23 SEQ ID NO:3.

FIG. 5(a) and (b) is the cDNA sequence for Isoform C of mouse CD23 SEQ ID NO:5.

FIG. 7 is the sequence alignment for the A and B forms of human CD23. Sequence from the line forward is identical for both types.

FIG. 10(a) and (b) is the cDNA sequence for the Alpha form of human CD23 position 186–800 for the region surrounding exon 3 (Isoform A) SEQ ID NO:7.

FIG. 12 is the cDNA sequence for Isoform C of human (CD23 position 186–800 for the region surrounding exon 3, the splice site is indicated SEQ ID NO:11.

FIG. 13 is the cDNA sequence for Isoform D of human CD23 B form position 66 to A form position 800 (B form position 686) for the region surrounding exon 3, the splice site is indicated SEQ ID NO:13.

DETAILED DESCRIPTION OF THE INVENTION

Figure 6:
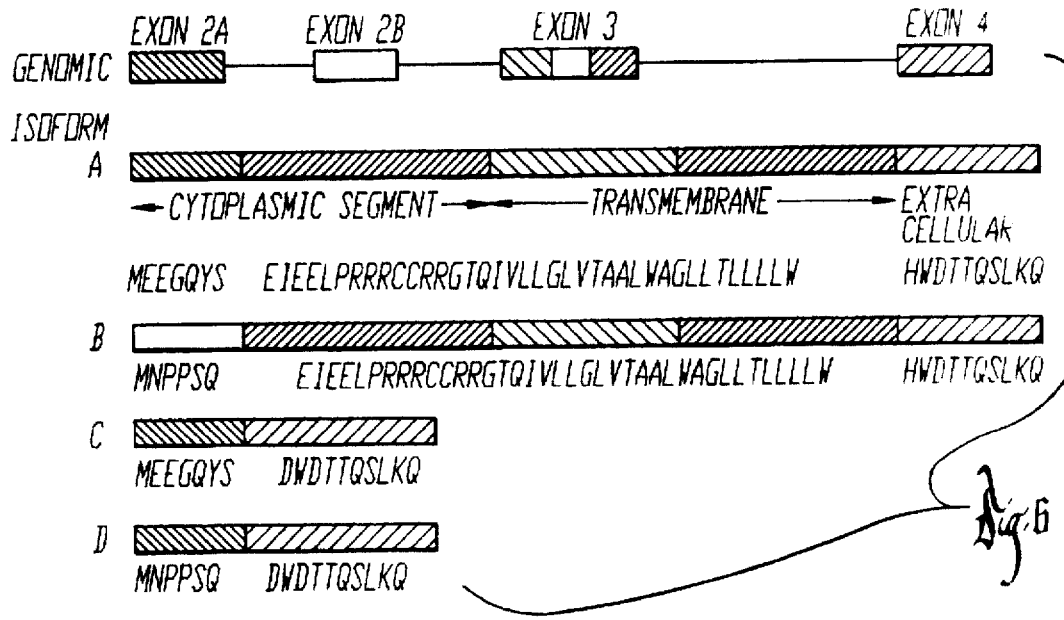
FIG. 6 is a schematic representation of human CD23 isoforms: Isoform A-SEQ ID NO:8, residues 1–55; Isoform B-SEQ ID NO:10, residues 1–54; Isoform C-SEQ ID NO:12, residues 1–17; Isoform D-SEQ ID NO:14, residues 1–16.

Applicant's invention relates to the unexpected discovery that the smaller soluble form of CD23 known to bind IgE exists not as an excised portion of the extra-cellular membrane bound CD23 but as a separately transcribed protein resulting from a mRNA transcript which omitted the exon coding for the transmembrane and a portion of the cytoplasmic segment CD23.

According to the present invention DNA sequences encoding on expression part or all of the amino acid sequences of human and mouse species soluble isoforms of CD23 have been isolated and characterized.

The DNA of human and mouse species origins were both subjected to similar procedures. For the mouse, cell lines of T and B lymphocytes were gathered from the thymus and spleen. From the human cells, cell lines were used from the American Type Culture Collection and from a gift of Dr. Junji Yodoi, from Kyoto University in Japan.

The cell lines were checked by staining with antibodies to detect the presence of CD23 and IgE binding activity. Then CD23 probes were synthesized from known sequences of CD23 and the known probes disclosed therein (Ikuta, et al, 1987, Cloning of cDNA for Human Lymphocyte Fce Receptor; Homology with Animal Lectins, *Proc. Natl. Acad. Sci USA* 84: 819–823); (Ludin, et al, 1987, Cloning and Expression of the cDNA Coding for a Human Lymphocyte IgE Receptor, *EMBO J.* 6: 109–114), and cellular mRNA was isolated and denatured. The denatured RNA was placed in solution along with the CD23 probe to identify CD23 mRNA. Finally a series of primers were constructed based on published sequences of CD23 and upon hybridization of the primer to the RNA template, reverse transcriptase was used to generate a cDNA copy of the mRNA. Isolation of the desired cDNA clone containing CD23 encoding DNA was accomplished through use of DNA-colony hybridization employing 32-P labeled CD23 probe earlier described. The resulting isolated DNA segments were then analyzed to determine DNA sequences. These isolated sequences provide the vehicles for large scale production of soluble CD23 which may be harvested for use in treatment of IgE mediated diseases such as asthma or other allergic responses as well as for models of study of IgE binding activity.

The following examples are presented by way of illustration of the invention and are specifically directed to procedures carried out prior to identification of CD23 encoding mouse cDNA clones and human genomic cDNA clones, to procedures resulting in such identification, and finally to the sequencing and to resulting development of expression systems and pharmaceutical carriers for therapeutic and in vitro use of produced soluble CD23.

EXAMPLE 1

Mouse CD23 Sequence Isolation and Purification

Cell line of adult mice B, T and macrophage lineage from the thymus and spleen were used for analysis, and mouse and monkey fibroblasts were used as controls. The cells were cultured in RPMI 1640 or Dulbecco media with 10% of Bovine calf serum at 37° C. with 7% of $CO_2$, and no mitogen was added to the culture.

Fresh preparations of thymocytes from AKR mice, and thymocyte and spleen cells from Balb/c mice were examined. WEHI 279, EL-4, CTL-2, J774, MC57, P388, 3T3, and COS, were obtained from ATCC, Gaithesburg, MD. R1.1 and Th9 was generously provided for D. Spinella, D10, was a gift from C. Janeway. CDC35 was a gift from D. Parker. CH1 was provided from 2C11 was provided from J. Bluestone. B53 was provided by Z Ovary. 1C9 is a clone isolated in this laboratory, in vitro—adapted and derived from the Balb/c thymic lymphoma Balentl-8. The cell lines used are listed in Table 1.

TABLE 1

| Murine cell lines | |
|---|---|
| WEHI 279 | B cell lymphoma |
| CH1 | B cell Ly 1b |
| D10 | Th2 cell |
| CDC35 | Th2 cell |
| IC9 | Thymic lymphoma line |
| EL4 | T lymphoma |
| CTL2 | T cell clone |
| R1.1 | T cell clone |
| Th9 | T cell clone |
| J774 | Macrophage cell line |
| MC57 | Myelomonocyte cell line |
| P388 | Macrophage cell line |
| B53 | Mouse Hybridoma anti-TNP IgE |
| C11 | Hamster Hybridoma anti-T3 |
| T3 | Mouse Fibroblast |
| OS | Monkey kidney Fibroblast |

Surface and Cytoplasmic Staining

T cell and B cell lines were stained on the surface and in the cytoplasm with monoclonal antibodies in order to detect CD23 and IgE binding activity. Biotinylated B3B4 (Rat IgG2a anti-murine CD23), FITC A3B1 (monoclonal IgEk murine anti-DNP), Biotinylated B53 (monoclonal IgEk murine anti-DNP) and 53-6.72, a non-related antibody (rat IgG2a) were used. The labeled cells were analyzed by FACS (Becton Dickinson FACS 440), and also manually observed in an Olympus microscope equipped with filters for fluorescein.

CD23 Probes

CD23 probes were synthesized by PCR using as template 10 ng of a Bluescript plasmid construction, containing the cDNA pL23.6 isolated by Kevin Moore, Bettler et al 1989 Molecular Structure and Expression of the Murine Lymphocyte FceRII PNAS 86: 7566–70, incorporated herein by reference.

RNA Analysis

Total cellular RNA was isolated by lysis of cells with denaturing solution (4M guanidium isothiocyanate, 24 mM sodium citrate pH 7.0, 0.5% sodium lauryl sarcosine, 0.1M 2-mercaptoethanol) in a ratio of 20 µl of denaturing solution per million cells. Sequentially additions were 0.1 volume of 2M Na acetate, 1 volume of phenol and 0.2 volumes of chloroform:isoamyl alcohol. After centrifugation at 10000 g the upper aqueous phase was precipitated with 1 volume of isopropanol, the pellet was resuspended in 0.3 initial volume of denaturing solution and an equal volume of isopropanol. The pellet was resuspended in 75% ethanol and sedimented. The dry RNA was dissolved in DEPC water, the OD measured, and a ratio A 260/A 280 of at least 1.7 was required for the RNA to be used.

Poly(a) mRNA was isolated with the Fastrack mRNA isolation kit (invitrogen, San Diego, Calif.).

Dot Blot of RNA

Total or poly (A) mRNA, was spotted onto Hybond membranes, with a 2 through 10 µg of RNA sample size being used, followed by dilutions. The membrane was baked at 80° C. for 2 hours, or UV crosslinked (Stratagene crosslinker), then put in Pre- and hybridization solution along with a CD23 probe. The washes were made with high stringency (0.1×SSC, 0.1% SDS, 30' at 62° C.) and the filter was placed with an X-ray film in a cassette with an intensifying screen, at −70° C. for variable periods of time. The signal intensity was measured by densitometry.

Primers

Eleven oligonucleotides were synthesized based on the published sequences of human and murine CD23 cDNA. Richard et al, *J. Immunol.* 147: 1067–1074 (1991) incorporated herein by reference. The primers were designed in order that each one had the highest homology in the 3' region between the cDNA of human and mouse B cells. The primers were used both for human and mouse experiments. None of the pairs formed primer dimers or exhibited self-annealing as determined by computer analysis of the sequences. The primer sequences are shown in Table 2. The primers were synthesized with an Applied Biosystem model 391 automated DNA synthesizer (Foster City, Calif.).

The first six primers are identical with the coding (sense) strand and the last four primers match the complementary (anti-sense) strand. An additional primer homologous with the B-isoform of human CD23 was also synthesized and used, (5'GCGGGGACGCAATAGAGTCAGAGGC 3'). The primers used and expected product sizes are depicted in FIG. 2 for murine and 8 for human.

cDNA Synthesis and Polymerase Chain Reaction (PCR)

The PCR reactions were set up with Ampli-Taq DNA Polymerase (Perkin Elmer), dNTPs, and 10X PCR buffer. The RNA template for the cDNA synthesis was 1 µg, but in some samples only 0.2 µg were used. M-MLV Reverse transcriptase and random hexamers were used for the first strand cDNA synthesis.

Immediately after the cDNA synthesis, 80 µl of PCR reaction mixture was added to the cDNA reaction along with 5 U. of Taq polymerase and 50 pM each of the 5'- and 3' primer. The mixture was put in a thermal cycler, (3 minutes at 94° C., annealing for 1 minute at 55 through 62° C., extension for 1 minute at 72° C., then 25 to 40 cycles, depending on the experiment, 1 minute 94° C., 1 minute 62° C. and 1 minute at 72° C. with 3 minutes of final extension. 10 to 20 µl of each amplification were separated by electrophoresis through agarose gel (1.5 to 3% in TBE), followed by staining with ethidium bromide. All the gels were blotted to Hybond membranes and then probed with a specific CD23 probe.

In some experiments a "nested" second round of PCR was performed using a template 10 µl of a 1:100 water dilution of the first PCR reaction. In most of the experiments two new internal primers were used to improve the specificity of the amplification. The second round of nested PCR was carried out for 25 to 30 cycles. In some samples only one internal primer was used. 10 to 20 µl of each reaction mixture was separated on agarose gels, stained with ethidium bromide and then the gels were blotted before being probed with a CD23 probe.

Southern Blots

PCR products were electrophoresed in 1.5 to 3% agarose in 1X TBE buffer. The concentration of agarose was varied

TABLE 2

Sequence of Primers

| Nucleotide Position in the murine cDNA SEQ ID NO:1 | Nucleotide sequence of primer | # |
|---|---|---|
| 164 | 5' CAAGACTGCCATGGAA 3' | (2)SEQ ID NO:1, residues 14–30 |
| 151 | 5' GGAAGGATCCAAACAAGACTGCCATGG 3' | (1)SEQ ID NO:1, residues 1–27 |
| 220 | 5' CGTTGCTGCTGTGCAAGACGTGGGACA 3' | (3)SEQ ID NO:1, residues 69–95 |
| 622 | 5' GGCTTGAATGAGAAGCGCACAGCCTCC 3' SEQ ID NO:1, residues 471–497 | |
| 850 | 5' AGCCAAAAGGAACAGGACTTCCTGATG 3' SEQ ID NO:1, residues 699–725 | |
| 1156 | 5' TTGGGGTGGGCCTTGTTGGAGTCACG 3' | (6)SEQ ID NO:1, residues 980–1005 (antisense) |
| 867 | 5' GTCCTGTTCCTTTTGGCTGTGGATGC 3' | (5)SEQ ID NO:1, 691–716 (antisense) |
| 786 | 5' GGAGCCCTTGCCAAAATAGTAGCAC 3' | (4)SEQ ID NO:1, residues 611–635 (antisense) |
| 448 | 5' GTGACATCTGAACAACCTGG 3' SEQ ID NO:1, residues 278–297 (antisense) SEQ ID NO:7 | | denotes the identification number of the primer.

depending on the size of the fragments to be analyzed. The gels were put in depurinating and denaturing solution, then transferred overnight to Hybond membranes, and then crosslinked by Stratagene Crosslinker. The filters were pre-hybridized and then hybridized with the 32-P labeled CD23 probe. The Random hexamer priming kit was used to label the CD23 probes.

DNA Sequence Analysis

The Applied Biosystems 373A automated DNA sequencer (Foster City, Calif.) was used to determine the DNA sequence of the PCR fragments generated. Both strands were sequenced by a Sanger-based dideoxy sequencing strategy, which used the taq polymerase as the enzyme and used fluorescent dye labeled terminators incorporated into the reaction. The use of different dye labels for each of the four bases allowed the sequences to be determined in a single lane, and detected as they migrated past a scanning argon laser positioned near the bottom of the polyacrylamide gel.

Metabolic Labeling and Immunoprecipitation of CD23 on Murine T- and B-Cell Lines Culture cells (10×10) were grown for 30 minutes in methionine-free RPMI 1640 without fetal calf serum, after discard this medium 10×106 cells/ml were grown for 6 hours in methionine free RPMI 1640 without fetal calf serum and supplemented with 100 uCi/ml (35S) methionine, the viability at the end was always greater than 90%. The cultures were spun and the supernatant and the cellular pellet processed in parallel experiments. The cells were washed 3X in PBS. 800 μl of boiling lysis buffer (2% SDS, 10x Tris, EDTA, 1.2M, NaCl, Triton 100) was added to the pellet, the DNA were sheared by repetitive passing through syringe. A column of 2 ml was completed with buffer (Tris, EDTA, NaCl, Triton). At 4° C., the lysate and the supernatant were precleared with agarose-streptavidin beads and with a non-related biotinylated antibody with same isotype (1:1000 dilution). Biotinylated B3B4 and IgE were used for the immunoprecipitation and the beads eluted with buffer Tris-Glycine pH 2.3, after neutralization the samples were boiled for 5 minutes in SDS-PAGE sample buffer, and loaded in a 15% PAGE. The dry gel or blotted to a nitrocellulose filter was exposed to autoradiographic films for variable periods of time.

EXAMPLE 2

Mouse RNA Analysis

Cellular RNA was analyzed with two different techniques: 1) Dot blot of total or Poly A RNA, and 2) cDNA synthesis through a Reverse Transcriptase procedure with amplification by PCR (Polymerase Chain Reaction).

The dot blot used serial dilutions of the samples, and hybridization with specific CD23 probes. The procedure used washing at very stringent conditions (0.1×SSC, 0.1 SDS, 30' at 62° C.). CD23 transcripts were detected in all the T cell samples examined except CTL2. The control samples (liver RNA, and 3 macrophage cell lines) were found to be negative for CD23 transcripts.

Reverse Transcriptase-polymerase Chain Reaction (RT-PCR)

After 30 cycles of RT-PCR the polyA RNA from CDC35, a T cell clone, which can be induced to express CD23 on its surface yielded a 622 bp product that was visualized on an ethidium bromide stained, agarose minigel. Under the same conditions, the macrophage cell lines were negative for CD23 and the PCR control that was run without template also was negative. The 622 bp product is the expected finding in murine B cells, but is a novel finding in murine T cells.

RT-PCR using primers 3 and 6 (See Table 2 for primer sequences), in a single round of PCR reaction (40 cycles), yielded a fragment of 936 bp, in 6 of 7 T cell samples visualized by Southern blot. Hybridization conditions and washes were very stringent (0.1×SSC, 0.1% SDS, 30' at 62° C.), and for detection a CD23 B cell cDNA probe was used.

To determine the structure of the 936 bp PCR product generated from T cells, it was initially isolated as the PCR product from CDC35, a T cell clone and in a series of nested amplifications, overlapping fragments were generated that spanned the full length of the 936 bp. These fragments were isolated and their nucleotide sequences were determined. A similar approach was taken with the RT-PCR products of the other T cell samples.

The cytoplasmic and transmembrane regions of CD23 from T and B cells were studied to discover any heterogenity in the 5' region as in human CD23. Specific primers for these regions were generated, and parallel experiments were carried using the same templates and experimental conditions. Primers 1 and 5 from Table 2 were used in an initial PCR reaction and 25 cycles of PCR were conducted.

The resulting T cell CD23-related products were shown to be heterogeneous on ethidium bromide stained gel electrophoresis. In 2 T cell sources (1C9 and THYMUS) up to 3 different PCR products were present, while in the other 2 samples (CDC35 and EL4), only a single PCR product was detected. The difference in molecular weight between the expected upper band of 716 bp (band 1) and the lower unexpected band of 596 bp (band 3) is 120 base pairs. The middle product (band 2) is approximately 50 base pairs smaller than the product in the expected upper band. Of the B cells, one line (WEHI 279) showed 3 bands, but the other B cell sample (B53), an IgE hybridoma, had a single band.

It is clear from these results (a) CD23-related transcripts are present in murine T cells as well as B cells; and (b) the patterns of CD23 transcripts observed are heterogeneous.

EXAMPLE 3

DNA Sequence Analysis of CD23 PCR Products

DNA sequence analysis were performed on bands 1, 2, and 3 of the PCR products generated from T and B cells. Band 1 from several murine T cell sources yielded a sequence that was identical to the published sequence of the B cell cDNA from nucleotide 1156 through 175 (amino acids 327 through 1) see FIG. 1 and FIGS. 3A and 3B, exon 3 is shown SEQ ID NO:1.

The DNA sequence was determined for the 3 cell lines producing the lower band (AKR, 1C9, and WEHI 279) (band 3). These three samples were found to be identical to each other. Compared to the published DNA sequence of B cell CD23, the sequence of each of these 3 samples showed a deletion of 120 bases. This was shown to be a deletion of exon 3, (nucleotide position 197 through 316). Because of the creation of a new splicing joint, between exon 2 and 4, there is a predicted change in amino acid from Histidine (cDNA position 48) to Aspartic Acid. (FIG. 1) Sequence at FIG. 4A and 4B SEQ ID NO:3.

Based upon the known sequence and function of the regions of CD23, deletion of exon 3 in some T- and B cells generated a transcript that no longer encoded the transmembrane segment or the anchor region of the cytoplasmic segment. This truncated transcript encodes on expression only the original amino acids 1 through 7 of the cytoplasmic tail which now is spliced to the original extra-cellular domain with the additional difference that position 48 changes from Histidine to Aspartic acid.

Figure 14A:
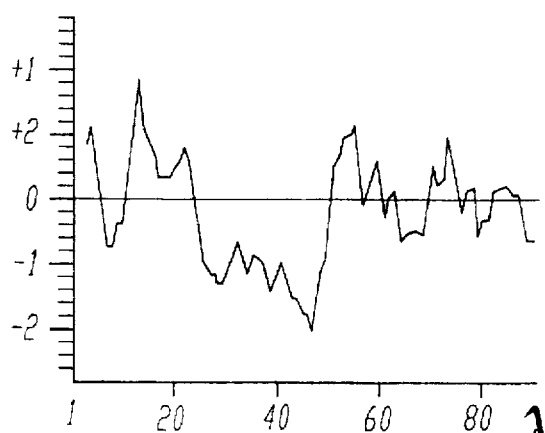
FIG. 14(a) and (b) is the hydrophilicity plot of Isoforms A and B of mouse CD23.
Figure 14B:
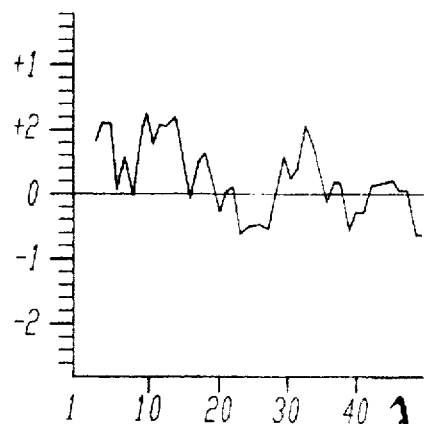

The Hydrophilicity profile of this truncated CD23-related product (FIG. 14) confirms that it is a soluble, secretory form of CD23. Soluble CD23, previously thought to occur by proteolysis has a number of functions including regulation if IgE, progression of B lymphocytes from G0 through G1 and in the differentiation of both early human myeloid precursors and Prothymocyte to Thymocyte. Purification and ultimately production of this protein would aid in the study of all of these processes.

The intermediate sized PCR product (band 2 FIGS. 1 and 5A and 5B) SEQ ID NO:5 has been characterized by DNA sequence analysis, PCR mapping and Molecular Weight analysis. The results of these studies show that this product lacks the anchor region of the cytoplasmic domain and the 5' half of the transmembrane segment. This transcript is generated by use of a cryptic splicing site at nucleotide positions 273 through 278 in the middle of exon 3. This truncated transcript contains the 3' portion of exon 3 that encodes the 13 hydrophobic amino acids of the membrane spanning segment of CD23. The predicted molecular weight of a product with such a splice fits well with the observed product generated in band 2 (FIGS. 1 and 5A and 5) SEQ ID NO:5. The physiological significance of this transcript is unknown, but it could encode a protein that assumes a different orientation, possibly that of a type I membrane protein.

EXAMPLE 4

Human CD23 Analysis Cell Lines

The human cell lines which were used in the present study were obtained from Dr. Junji Yodoi, Kyoto University, and from the American Type Culture Collection (ATCC, Rockville, Md.).

The cell lines are listed in Table 2.

TABLE 2

Human Cell Lines

| Cell Line | Characteristics |
|---|---|
| 8866 | B cell line, Epstein Barr Virus Transformed, Lamson et al. J. Immunol. 125:293 (1980) |
| MT-2 | T cell line, CD4+, HTLV+, Cord Origin, Miyoshi et al., Nature 294:770–771 (1981) |
| MT-1 | T cell line, CD4+, HTLV+, Miyoshi et al Gann 72:978–81 (1981) |
| ED | T cell line, HTLV+, Maeda et al J. Exp. Med. 162:2169–74 (1986) |
| ATL-2 | T cell line, HTLV+, Maeda et al J. Exp. Med. 162:2169–74 (1986) |
| MOLT4 | T cell line, ALL, HTLV−, Sugamara et al Int. J. Cancer 34:221–28 (1984) |
| JURKAT | T cell line, ALL, HTLV−, Sugamara et al Int. J. Cancer 34:221–28 (1984) |
| U937 | Monocyte Like Cell Line, Ralph et al. J. Exp. Med. 143:1528 (1976) |

There are A and B forms of CD23 in human B lymphocytes and these differ in amino acid sequence in only the first six amino acids of their intraplasmic portions, due to alternate exon usage. (See FIG. 6). The A form encodes the first 7 amino acids different while the B form's first 6 amino acids are different. The remainder of the amino acid and cDNA sequence is identical. The cDNA's of the two forms differ not only in the first 6 amino acids they encode but also in the 5' non-translated region of cDNA. The A form non-translated region is significantly longer, approximately 185 non translated bases with the coding region beginning at position 186. The B form has 65 non-translated bases and the coding region begins at position 66. FIG. 7 depicts the cDNA's of the A and B forms aligned for comparison SEQ ID NOS:7 and 9, respectively. The sequences downstream of the vertical line of both cDNA's are identical. The Alpha form is constitutively expressed on B lymphocytes, whereas the Beta form is induced by Interleukin 4 of B lymphocytes and other cells.

Measurement of Soluble CD23

Soluble CD23—(defined as CD23 not cell-bound and present in culture supernate)—was detected by an Enzyme-linked immunosorbent assay (ELISA). A sandwich procedure was used with two monoclonal anti-CD23 antibodies specific for different epitopes on CD23.

The cell lines 8866 and MT-2 in a concentration of 1×10 cells/ml were cultured in media, at 37° C. for 72 hours. The cell viability at 72 hours of culture was below 50% then 80 ml of the supernatant was collected, cooled to 4° C., and concentrated by ultra centrifugation using a Millipore filter (exclusion cut-off, 10,000). The concentrate was fractionated with a millipore filter (exclusion cut-off, 30,000), and the retentate was refiltered through a new 30,000 cut-off filter. Immediately after concentration, 2 ml of concentrate was analyzed for the presence of CD23 by immunoassay.

A 96-well plate (Immunolon II, Dynatech Laboratories, Inc.) was coated with 100 μl/well of 2 μg/ml of purified anti-CD23 monoclonal antibody in 0.1M carbonate buffer (pH 9.6) at 4° C. overnight. The wells were then washed with PBS containing 0.05% Tween 20, 0.1% bovine serum and coated with PBS containing 2% BSA for 3 hours at 37° C. The wells were washed and samples were added to each well. Each sample was processed in triplicate undiluted or at dilutions of 1:2, 1:4, and 1:8. 50 μl of sample was added to each well and incubated at 37° C. for 3 hours. The plates were washed, and 50 μl of bio-conjugated anti-CD23 monoclonal antibody was added to each well. The plates were incubated 3 hours at 37° C, washed and incubated with 50 μl of alkaline phosphatase-conjugated avidin (Cappel, West Chester, Pa.), incubated at 4° C. for 3 hours, washed and incubated with 1 mg/ml phosphatase substrate (Sigma Diagnostics, St. Louis, Mont.) for 45 minutes at room temperature. The A 405 was determined with a Microplate Autoreader (Biotech Instruments), the data were analyzed with Lotus 1-2-3 for Windows Release 1.0 (Lotus, Cambridge, Mass.), and the graphics were developed with Lotus Freelance Graphics for Windows, Release 1.0 (Lotus). Recombinant human soluble CD23 was used as the reference standard and for quality control. The sensitivity of this assay was determined to be 2 ng/ml.

CD23 Probes

Figure 9:
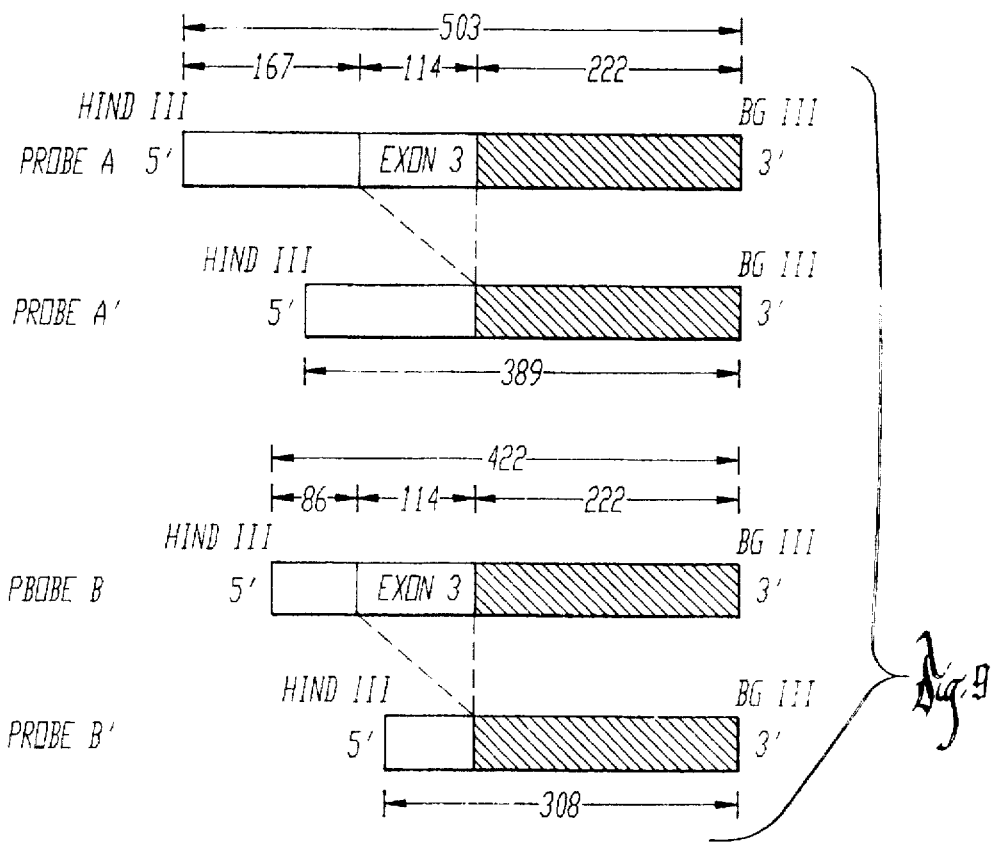
FIG. 9 is a schematic illustrating the probes used to detect human CD23 alpha and beta isoforms.

CD23 probes were synthesized by PCR using a template 10ng of a Bluescript plasmid construction containing cDNA pL23.6. One probe specific for the A and B form and each truncated product was used. See FIG. 9 SEQ ID NOS:7 and 9.

Reverse transcriptase-Polymerase Chain Reaction

The poly A mRNA of the cell lines was extracted using either, the Fastrack kit (Invitrogen) or QuickPrep kit (Pharmacia). Synthesis of first strand and PCR were done in the same manner as for the mouse experiments. The only difference was that in the human studies, a "hot start" protocol was used. Briefly, the tubes with a mixture of CR buffer, primers, and dNTP, were put at 80° C., the template was added, and then the taq Polymerase was added. The cycle program and conditions were the same as described for the murine studies.

DNA Sequence Analysis

The procedure was the same as for the mouse analysis; the primers used for the human studies were synthesized as discussed based on the published cDNA sequence of the Human A and B form of CD23 as earlier described and homology with the mouse forms. Yokota et al. Two Species of Human Fce Receptor H (FcerII/CD23): Tissue-Specific and Il-4 Specific Regulation of Gene Expression 65 *Cell* 611–18 (1988), incorporated herein by reference, and in Genbank Accession number M23562 SEQ ID NO:7 (position 112–1037) A form and SEQ ID NO:5 (position 7–1025) B form.

The primers used for the human studies are listed in Table 4, along with their hybridization position in the A for cDNA.

shown in FIG. 6). The PCR products were visualized in the agarose ethidium bromide stained gel. Using the same primers and experimental conditions, the T cell samples MT-1, MT-2, ATL-2, ED, MOLT4, and the eosinophil cell line EOL3 were negative.

b) Using the 5' primer specific for the B form of human CD23 which hybridizes to cDNA position 1–25 of the B form cDNA and the same 3' primer, primer 5 (which hybridizes to position 784–809 of the A form which corresponds to position 661 and 686 of the B form), the B cell line 8866 yielded a product of 686 bp, which is the expected size. However, two additional and unexpected products were generated, and were approximately 572 bp and 610/620 bp in size (not shown in FIG. 6).

c) The eosinophil cell line EOL3 also yielded a 686 bp product. This is a novel result, because it is the first time that by RT-PCT, the B form of CD23 has been identified in human eosinophil cells.

d) Through the use of the 5' primer specific for the B form, the T cell line MT-2 yielded a product of 686 bp, which is the expected result for B cells, but is a novel finding in T cells, and another band of 572 bp.

These results show that mRNA of the A form of human CD23 is expressed in the human B cell line 8866 and that two additional A form related transcripts are also present.

These results also show that mRNA of the B form of human CD23 is expressed in the B cell line 8866, the T cell

TABLE 4

Sequence of Primers

| Nucleotide Hybridization Position (cDNA) | Nucleotide sequence of primer | # |
| --- | --- | --- |
| 7 (B form) | 5' GCGGGGACGCAATAGAGTCAGAGGC 3' | B(SEQ ID NO:9, residues 1–25 |
| 163 (A form) | 5' GGAAGGATCCAAACAAGACTGCCATGG 3'<br>5' GTGACATCTGAACAACCTGG 3'<br>hybridizes with SEQ ID NO:7,<br>residues 323–342 (antisense) | 1 hybridizes with SEQ ID NO:7, residues 52–78 |
| 728 (A form) | 5' GGAGCCCTTGCCAAAATAGTAGCAC 3' | 4 hybridizes with SEQ ID NO:7,<br>residues 593–617 (antisense) |
| 784 (A form) | 5' GTCCTGTTCCTTTTGGCTGTGGATGC 3' | 5 hybridizes with SEQ ID NO:7, residues 1–25 (antisense) |

Figure 8:
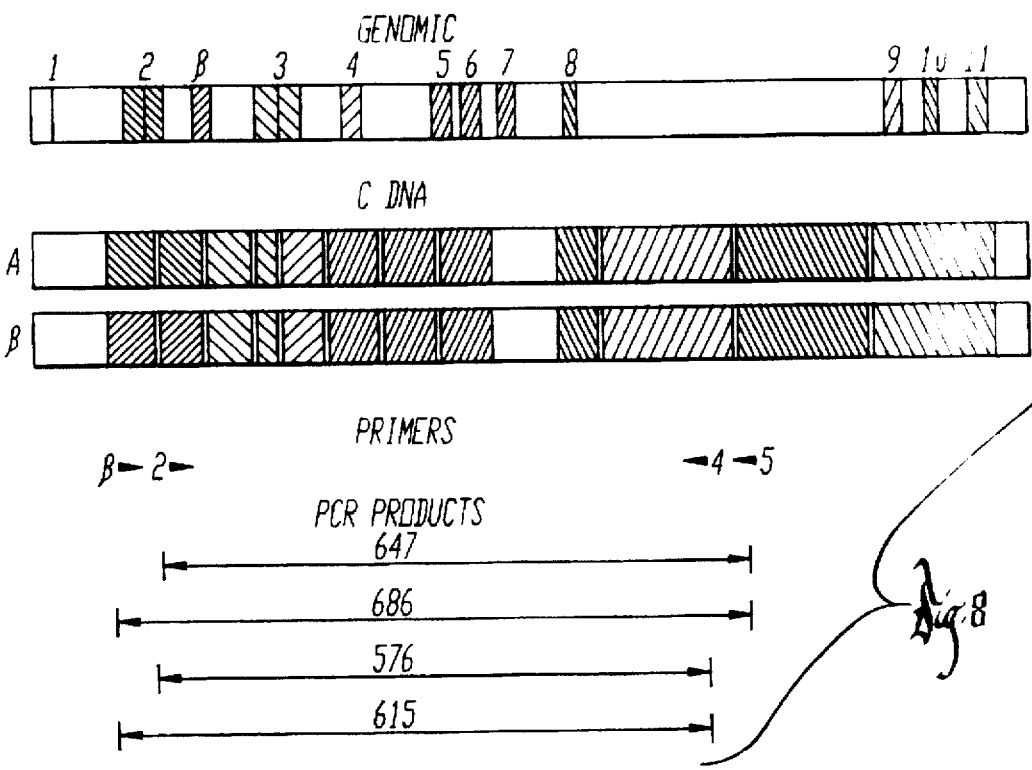
FIG. 8 is a schematic illustrating the primers and expected PCR products for human CD23.

The first two primers are identical with the coding (sense) strand and the last three primers match the complementary (anti-sense) strand. Primer #3 was only used for sequence purposes. The (#) denotes the identification number of the primer and its site of binding is shown. See FIG. 8 for PCR primers and expected amplification products.

EXAMPLE 5

RNA Analysis RT-PCR Results

RT-PCR of B- and T-cell line mRNA with the primers previously discussed that identify the A and B forms of human CD23 (FIG. 6):

a) Using a 5' primer for the A form of human CD23, (primer 1) which hybridizes to sequence position 163–189 of the A form cDNA SEQ ID NO:7 and common 3' primer, primer 5 which hybridizes to sequence position 784–809 of the A form cDNA, the B cell line 8866 yielded a product of 647 bp, which is the expected amplification size with the primers for a CD23 product including exon 3. However, two additional and unexpected products were detected, one of 533 bp and the second of approximately 570/580 (not line MMT-2 and the eosinophil line EOL-3. Additional B form-related transcripts were identified in the B cell line 8866, and in the T cell line MT-2, MT-1.

In order to improve the specificity and sensitivity of the PCR technique, a "nested" PCR technique was also used. A new 3' primer, primer 4 (which hybridizes cDNA position 704–728 of the A form), located 71 bp upstream of the 3' primer used for the first round of PCR, was used in the nested second round. The results of the nested experiments for the A form of the human CD23 are the following:

a) With primers specific for the human A form of CD23 cells the 8866 cell line yielded four PCR products. The expected 576 bp product (647–71) for the human CD23 A form was generated, but additional products were present of 462 bp, and 500 bp. These products are as expected 71 bp shorter than the other truncated products generated by the single round of PCR. This smaller size reflected that the priming site of the new internal 3' primer was 71 bp upstream of the original 3' priming site.

b) With primers specific for the A form of human CD23 the EOL 3 cell line yielded a single product of 462 bp.

The products of 501 and 576 bp detected in B cells were not detected in the eosinophil cell line.

c) The T cell lines were negative.

The result for the B form of human CD23 in the nested PCR experiments are as follows:

a) The 8866 cell line yielded 3 PCR products. One was a 615 bp product (the expected amplified size). In addition 501 bp and 540/550 bp fragments were present and correlate with the observation of the two additional products generated during 25 cycles of a single round of PCR (533 and 570/580). The smaller size reflects that the priming site in the nested PCR for the internal 3' primer is 71 bp upstream from the original priming site.

b) In the nested PCR the EOL-3 line yielded 3 products, the expected product of 615 bp, and unexpected products of 501 bp and 540/550 bp. This result is the same as the result with the B cell line.

c) The T cell lines MT-2 and ED yielded a product of 615 bp, the expected amplified size for B cell CD23, but a novel result in T cells. One T cell line also showed two additional products of 501 bp and 540/550 bp.

d) The T cell line MT-1 yielded a product of 501 bp.

e) The T cell line ATL-2 was negative for B Form CD23 transcripts, even in the nested PCR.

Thus the presence of truncated CD23 products correlates with RT-PCR an assay 100 times more sensitive than RNA protection assays and nested PCR which is up to 10 times more sensitive than RT-PCR. Table 5 depicts the PCR products as they correlate through both tests. See also FIGS. 8 and 6.

TABLE 5

|  | Isoform A<br>A form<br>expected | Isoform B<br>B form<br>expected | Isoform C<br>A form<br>minus<br>exon 3 | Isoform D<br>B form<br>minus<br>exon 3 |
| --- | --- | --- | --- | --- |
| RT-PCR | 647 bp | 686 bp | 533 bp | 572 bp |
| Nested PCR<br>(X-71) | 576 bp | 615 bp | 462 bp | 501 bp |

EXAMPLE 6

DNA Sequence Analysis of Human CD23

The sequences of the 647 bp and 576 bp PCR generated products from the B cell line 8866 were found to be identical to the published sequence of the A form of CD23. See FIG. 10 illustrating this sequence position 186–800. The 533 and 462 bp product was also identical to CD23 sequence from which the full length of exon 3 had been deleted. The newly formed splicing site between exon 2 and 4, resulted in a change in the predicted amino acid sequence encoded by this transcript, with a substitution of Histidine for Aspartic acid. See FIGS. 10 and 12.

In 8866 and EOL 3, a 462 bp nested PCR generated product also was shown to be a truncated transcript from which had been deleted all of exon 3. This truncated form of CD23 lacked all of the transmembrane segment and a portion of the cytoplasmic tail. These exon 3-deleted, truncated transcripts encode proteins that are a soluble form of CD23.

The sequences of the fragments generated with primers specific for the B form of human CD23 showed that, the 686 bp product from the 8866, EOL 3, and MT-2 were identical to the sequence published for the B form of CD23. These findings are expected for the B cells, but the eosinophil cell line, and for the T cell line are novel.

Figure 11B:
FIG. 11(a) and (b) iS the cDNA sequence for the Beta form of human CD23 B form position 66 to A form position 800 (B form position 686) for the region surrounding exon 3 (Isoform 13) SEQ ID NO:9.

Nucleotide sequence analysis of the 615 bp nested PCR products generated from the B cell line (8866), the eosinophil cell line (EOL-3), and the T cell lines (MT-2 and ED) showed that these products are identical with the published sequence of the B form of CD23. See FIG. 11 (B form cDNA position 66 through A form position 800). This is the expected result for a B cell, but is a new finding for eosinophil and T cell lines.

Nucleotide sequence analysis of the 572 bp fragments from the B cell line and from one T cell line, and the 501 bp nested PCR generated fragment from the B cell line, the eosinophil cell line, and the T cell lines, all showed that this transcript has a deletion of the entire exon 3. See FIG. 13. In addition to the exon 3 deletion, there is a predicted Histidine → Aspartic change at position 45.

Evidence for the heterogeneity of human CD23 beyond the presence of A and B forms, is suggested by the RT-PCR experiments and sequence analysis. Those findings show that the B cell line as well as the T cell lines and the eosinophil line, all have additional CD23-related transcripts. One of these transcripts is a truncated form of CD23 with complete deletion of exon 3. The deletion of exon 3 would result in a transcript, which encodes a CD23 protein that would not be membrane bound and is released as soluble CD23.

EXAMPLE 7

Production of Soluble CD23 Proteins

Once the gene sequence for CD23 had been purified and isolated a number of recombination techniques generally known and commonly practiced in the art of molecular biology can be used to produce mass quantities of this polypeptide. The first technique involves creating plasmid shuttle vector. In this technique a bacterial plasmid such as PBR 322 which contains ampicillin and tetracycline resistance genes is cut with restriction enzymes and the desired foreign DNA fragments, here the soluble form CD23 DNA segments, are taken up by the plasmid. The plasmid vectors can then be transformed into the recipient bacterial hosts such as E. coli in the presence of PEG to allow expression by the bacteria of the inserted foreign DNA fragments.

Another integrative strategy involves placement of the foreign DNA desired sequence into a bacteria phage lambda vector. Once the foreign gene is inserted the phage is allowed to infect and transform a desired host cell, once again allowing the host to express the foreign DNA soluble CD23 gene.

Through use of these integrative strategies, bacterial host cells can be transformed to contain the human or mouse form of soluble CD23 and can express and produce this protein. Because of the very high replication rate for bacteria, great quantities of the desired protein can be reproduced by these methods.

Figure 15:
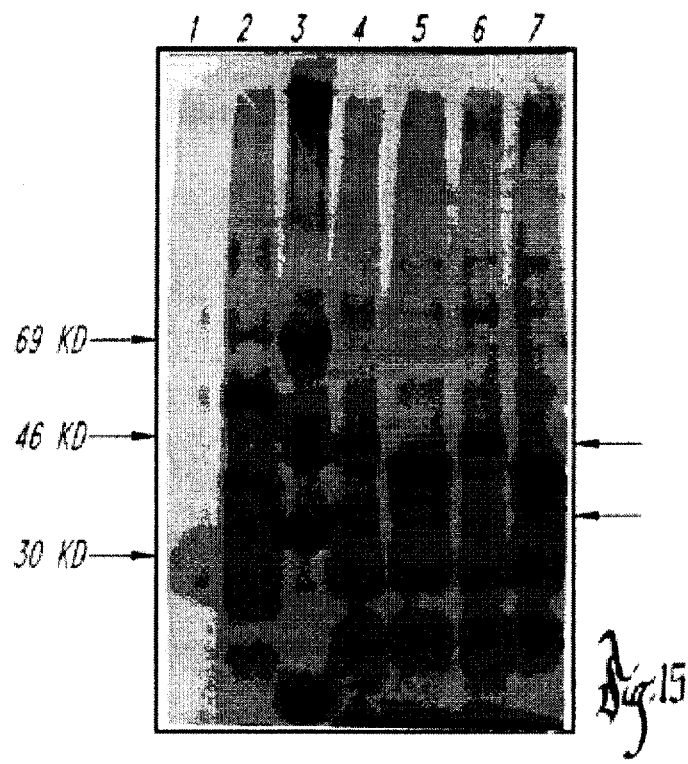
FIG. 15 depicts the de-teEction of CD23/FceRII isoform proteins produced in vitro Lane 1; negative control (no RNA). Lane 2: positive control (Xenopus elongation factor 1-α RNA, 50 kDa), lane 3: molecular size marker, Lane 4: CD23/FceRII type a, Lane 5: CD23/FceRII type a', Lane 6: CD23/FceRII type b, Lane 7: CD23/FcePII type b'. The molecular sizes are indicated on the left.

In vitro translation (FIG. 15)

Four types of CD23 /FcεRII cDNA's (Isoform A, B, C and D) were subcloned in Bluescript II at EcoRI site. These vectors were linearized by XhoI digestion and in vitro transcription reactions were performed using T3 RNA polymerase. The uncapped transcripts were translated with [$^{35}$S] methionine using "Ambion Retic Lysate IVT™ Kit in vitro Translation Kit" following the manufacturer's instructions.

2.5 μl of the samples diluted with 10 μl of 2.5% SDS sample buffer were subject to SDS-PAGE analysis. The gel was dried on Whatman chromatography paper and subjected to autradiography. The four types of CD23/FceRII protein were detected at expected sizes.

Production of anti-CD23/FceRII serum 1.0 mg of recombinant 25 kDa CD23/FceRII emulsified with complete Freund's adjuvant was subcutaneously injected to three rabbits as immunogen. Moreover, twice boosts were performed every 2 weeks using the same amount of antigen emulsified with incomplete Freund's adjuvant. Seven days after the final boost, their blood were collected through the catheters placed in the carotid arteries.

Titration of the sera for anti-recombinant 25 kDa CD23/FceRII polyclonal antibody Fifty microliters of 5 μg/ml recombinant 25 kDa CD23/FceRII was added to each well of a 96-well E1A plate (Corstor 3590, Corstor) and incubated at 37° C. for 1 hour. After washing, each well was incubated with 200 μl of PBS containing 3% skim milk (Morinaga) at 37° C. for 1 hour. The rabbit sera were serially diluted with PBS containing 1% of skim-milk and added to the antigen-coated plates. After incubation at 37° C. for 2 hours, 50 μl of 2,000-fold diluted alkaline phosphatase (ALP) conjugated goat anti-rabbit IgG was added and incubated at 37° C. for 1 hour. The enzyme reaction was initiated by adding 50 μl of 1.0 mg/ml of o-Phenylene diamine solution. The titer of captured anti-recombinant 25 kDa CD23/FceRII polyclonal antibodies was assessed at OD 490 nm by microplate reader (Molecular Devices, Wako). The sear from the 3 rabbits were all found to react with the recombinant 25 kDa CD23/FceRII even after the 270,000-fold dilutions.

Figure 16:
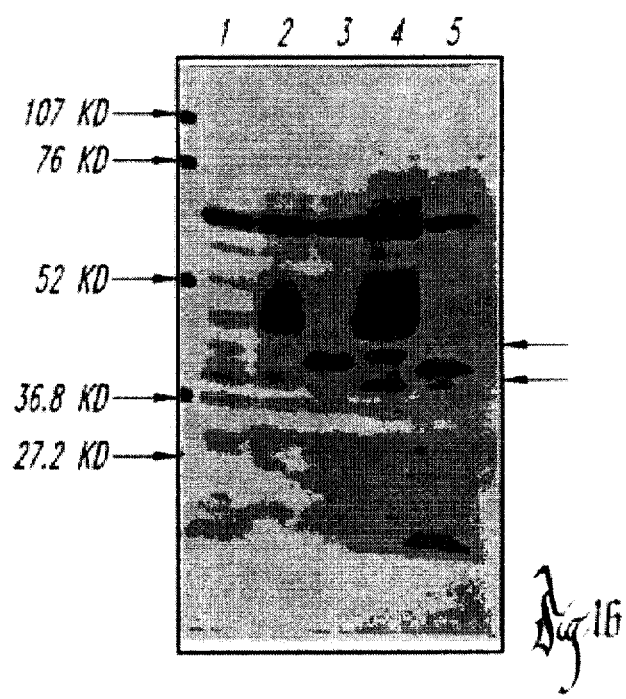
FIG. 16 is a Western blot analysis of CD23/FceRII isoforms expressed in COS-7 cells lane 1: control vector, lane 2: CD23 type a, lane 3: CD23 type a', lane 4: CD23 type b, lane 5: CD23 type b', The molecular size markers are indicated on the left.

Expression in COS cell (FIG. 16)

The four types of CD23/FceRII cDNA's were subcloned under the control of SV40 promoter. COS-7 cells were transfected with 10 μg of each expression vector by electroporation using GenePulser (BioRad). After 72 hours, the cells were harvested and assayed for the level of CD23/FceRII expression. Lysates of COS-7 cells solubilized in 0.5% Nonidet P 40 were electrophoresed on a 10% polyacrylamide gel under non-reduced conditions. After electrotransfer to a polyvinylidene difluoride (PVDF) membrane (Millipore), the membrane was blocked with PBS containing 3% skim-milk, and incubated at 37° C. for 2 hours with 2,000-fold diluted anti-CD23FceRII serum. Horseradish peroxidase labeled anti-rabbit IgG was used as the secondary antibody. The bands reactive with the serum were visualized by horseradish peroxidase-ECL method (Amersham). The four types of CD23/FceRII isoforms were detected at expected sizes.

EXAMPLE 8 (Prophetic)

Pharmaceutic and Therapeutic Methods

Based upon the known activity of CD23 and the encoded regions harvested soluble form CD23 could be used in treatment of IgE mediated diseases such as asthma, allergic responses, and reaction to some parasites. As previously discussed the soluble CD23 contains the entire binding region and merely omits the membrane anchoring region. An appropriate pharmaceutical vehicle would be selected from such forms as a pill, isotonic injection, or saline solution form which may be introduced into the system of the affected patient.

Pharmaceutically acceptable vehicles are materials useful for the purpose of administering the harvested CD23, which may be solid, liquid or gaseous materials, which are otherwise inert and medically acceptable and are compatible with the active ingredients.

These pharmaceutical compositions may be given orally, intravenously, through injections of IV solutions, or subcutaneously. Recommended dosages of IgE would likely be a very small quantity of a nanogram or less. The dose would be commensurate with an effective amount to achieve the desired regulatory response, depending on the amount of excess IgE in the patients septum. Since this protein is soluble and naturally occurring it will likely exhibit no toxicity to humans. Depending on the nature of the disease it is likely that more than one dosage will be needed, perhaps on a regular basis to regulate IgE.

Additional soluble form CD23 present in the system could then interact to turn off IgE thereby relieving the patients from the allergic responses mediated by IgE. This process of interaction of IgE with membrane bound CD23 has been demonstrated in the art, (Nelms et al, Enhanced Medeated Suppression of Epsilon Heavy Chain Gene Expression and a Murine IgE Producing Hybridoma, *Molecular Immun. vol.* 28 pp. 599–606 (1991)). In this paper a cancel cell was used with an IgE cell to make a hybridoma which produces IgE. This hybridoma was then exposed to T cells containing CD23. The T cells interacted with the hybridoma resulting in turning off heavy chain of IgE demonstrating that CD23 can react to suppress IgE synthesis. Thus, introduction of the soluble CD23 into the system of affected patients will likely generate a similar response and shut off synthesis of IgE.

Additional uses for this protein include models to study mechanisms of IgE binding, as also to screen other molecules for their biological activity with soluble CD23 both in vivo and in vitro as earlier described.

---

What is claimed is:

1. A purified and isolated nucleic acid molecule which codes upon expression a soluble isoform of CD23, said nucleic acid molecule selected from the group consisting of: SEQ ID NO:3, SEQ ID NO:5, SEQ ID NO:11 and SEQ ID NO:13.

2. The nucleic acid molecule of claim 1 wherein said nucleic acid molecule has a sequence consisting of SEQ ID NO:3.

3. The nucleic acid molecule of claim 1 wherein said nucleic acid molecule has a sequence consisting of SEQ ID NO:5.

4. The nucleic acid molecule of claim 1 wherein said nucleic acid molecule has a sequence consisting of SEQ ID NO:11.

5. The nucleic acid molecule of claim 1 wherein said nucleic acid molecule has a sequence consisting of SEQ ID NO:13.

6. A procaryotic or eucaryotic host cell transformed or transfected with the nucleic acid molecule of claim 1 in a manner allowing the host cell to express soluble CD23.

7. A biologically functional circular plasmid or viral DNA vector including the nucleic acid molecule of claim 1.

8. A procaryotic or eucaryotic host cell stably transformed or transfected with a DNA vector according to claim 7.

\* \* \* \* \*